United States Patent
Widdison

(10) Patent No.: US 9,999,680 B2
(45) Date of Patent: Jun. 19, 2018

(54) CONJUGATES COMPRISING CELL-BINDING AGENTS AND MAYTANSINOIDS AS CYTOTOXIC AGENTS

(71) Applicant: ImmunoGen, Inc., Waltham, MA (US)

(72) Inventor: Wayne C. Widdison, Belmont, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days. days.

(21) Appl. No.: 14/763,608

(22) PCT Filed: Feb. 28, 2014

(86) PCT No.: PCT/US2014/019502
§ 371 (c)(1),
(2) Date: Jul. 27, 2015

(87) PCT Pub. No.: WO2014/134483
PCT Pub. Date: Sep. 4, 2014

(65) Prior Publication Data
US 2015/0359903 A1 Dec. 17, 2015

Related U.S. Application Data

(60) Provisional application No. 61/770,794, filed on Feb. 28, 2013.

(51) Int. Cl.
| | | |
|---|---|---|
| *A61K 47/48* | (2006.01) | |
| *A61K 31/5365* | (2006.01) | |
| *C07D 213/71* | (2006.01) | |
| *C07D 257/08* | (2006.01) | |
| *C07D 401/12* | (2006.01) | |
| *C07D 498/18* | (2006.01) | |
| *A61K 47/68* | (2017.01) | |

(52) U.S. Cl.
CPC .... *A61K 47/48384* (2013.01); *A61K 31/5365* (2013.01); *A61K 47/6803* (2017.08); *A61K 47/6851* (2017.08); *C07D 213/71* (2013.01); *C07D 257/08* (2013.01); *C07D 401/12* (2013.01); *C07D 498/18* (2013.01)

(58) Field of Classification Search
None
See application file for complete search history.

(56) References Cited

U.S. PATENT DOCUMENTS

2012/0253021 A1  10/2012  Li et al.

FOREIGN PATENT DOCUMENTS

WO    2009/134977 A1    11/2009

OTHER PUBLICATIONS

CAS RN 27846-30-6 (entered into STN Nov. 16, 1984).*
CAS RN 915798-83-3 (entered into STN Dec. 18, 2006).*
CAS RN 244141-18-2 (entered into STN Oct. 13, 1999) (Year: 1999).*
Sun et al.; "Design of Antibody-Maytansinoid Conjugates Allows for Efficient Detoxification via Liver Metabolism"; Bioconjugate Chemistry; 22(4):728-735 (2011).
Phillips et al.; "Targeting HER2-Positive Breast Cancer with Trastuzumab-DM1, an Antibody-Cytotoxic Drug Conjugate"; Cancer Research; 68(22):9280-9290 (2008).
Kellogg et al.; "Disulfide-Linked Antibody-Maytansinoid Conjugates: Optimization of In Vivo Activity by Varying the Steric Hindrance at Carbon Atoms Adjacent to the Disulfide Linkage"; Bioconjugate Chemistry; 22(4):717-727 (2011).
Erickson et al.; "Tumor Delivery and In Vivo Processing of Disulfide-Linked and Thioether-Linked Antibody-Maytansinoid Conjugates"; Bioconjugate Chemistry; 21(1):84-92 (2010).
Erickson et al., Antibody-maytansinoid conjugates are activated in targeted cancer cells by lysosomal degradation and linker-dependent intracellular processing. Cancer Res. Apr. 15, 2006;66(8):4426-33.
Flygare et al., Antibody-drug conjugates for the treatment of cancer. Chem Biol Drug Des. Jan. 2013;81(1):113-21.
Zhao et al., Synthesis and evaluation of hydrophillic linkers for antibody-maytansinoid conjugates, J Med Chem. May 26, 2011;54(10):3606-23.

* cited by examiner

*Primary Examiner* — Craig D Ricci
(74) *Attorney, Agent, or Firm* — McCarter & English, LLP; Yu Lu; Xin Zhang

(57) ABSTRACT

The invention provides linker compounds containing a disulfide group, and maytansin-derived cytotoxic compounds that are useful for forming a CBA-drug conjugates, and conjugates so formed. Such conjugates and/or cytotoxic compounds may be effective for treating a range of diseases, such as cancer, with a relatively high activity at a relatively low, non-toxic dose.

5 Claims, No Drawings

CONJUGATES COMPRISING CELL-BINDING AGENTS AND MAYTANSINOIDS AS CYTOTOXIC AGENTS

REFERENCE TO RELATED APPLICATIONS

This application is a U.S. national stage filing under 35 U.S.C. § 371 of International Application No. PCT/US2014/019502, filed on Feb. 28, 2014, which claims the benefit of the filing date, under 35 U.S.C. § 119(e), of U.S. Provisional Application No. 61/770,794, filed on Feb. 28, 2013, the entire contents of each of which are incorporated herein by reference.

BACKGROUND OF THE INVENTION

Antibody-drug conjugates (ADC) and cell binding agent-drug conjugates are emerging as a powerful class of anti-tumor agents with efficacy across a range of cancers. Cell binding agent-drug conjugates (such as ADCs) are commonly composed of three distinct elements: a cell-binding agent (e.g., an antibody); a linker; and a cytotoxic moiety. The linker component of ADC is an important element in developing targeted anti-cancer agents that possess an optimal therapeutic window, i.e., therapeutic activity at a low, non-toxic dose.

Therefore, there is a need for targeted therapies such as ADCs and other cell binding agent-drug conjugates having a new class of linker components.

SUMMARY OF THE INVENTION

A first embodiment of the invention features a conjugate represented by the following formula, or a pharmaceutically acceptable salt thereof:

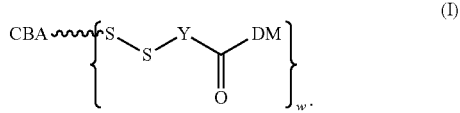

(I)

In Formula (I) above, CBA is a cell binding agent; DM is a drug moiety represented by the following formula:

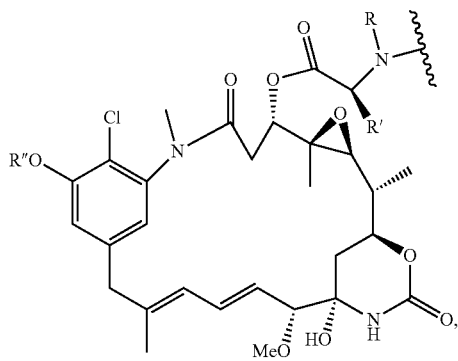

(II)

in which R, R', and R'', for each occurrence, are independently H or an optionally substituted alkyl; Y is $-(CR_3R_4)_n CR_1R_2-$; $R_1$ to $R_4$, for each occurrence, are independently H, an optionally substituted alkyl, an optionally substituted alkenyl, an optionally substituted cycloalkyl, an optionally substituted heterocyclyl, an optionally substituted aryl, or an optionally substituted heteroaryl; n is an integer between 0 and 15; and w is an integer between 1 and 20. In one embodiment, for conjugates of formula (I), CBA does not comprise a modified lysine amino acid residue carrying a free thiol (—SH) group, wherein the free thiol group is used to conjugate with the cytotoxic compound of the present invention.

A second embodiment of the invention features a conjugate represented by the following formula, or a pharmaceutically acceptable salt thereof:

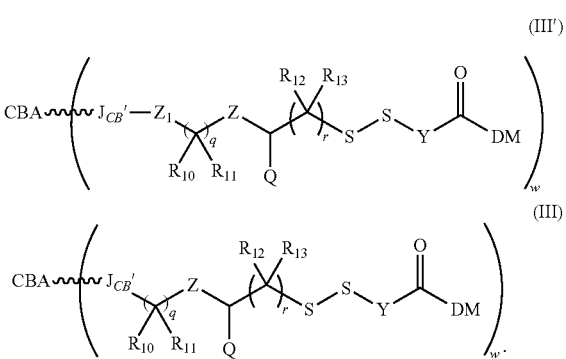

In Formula (III) or (III') above, $J_{CB'}$ is

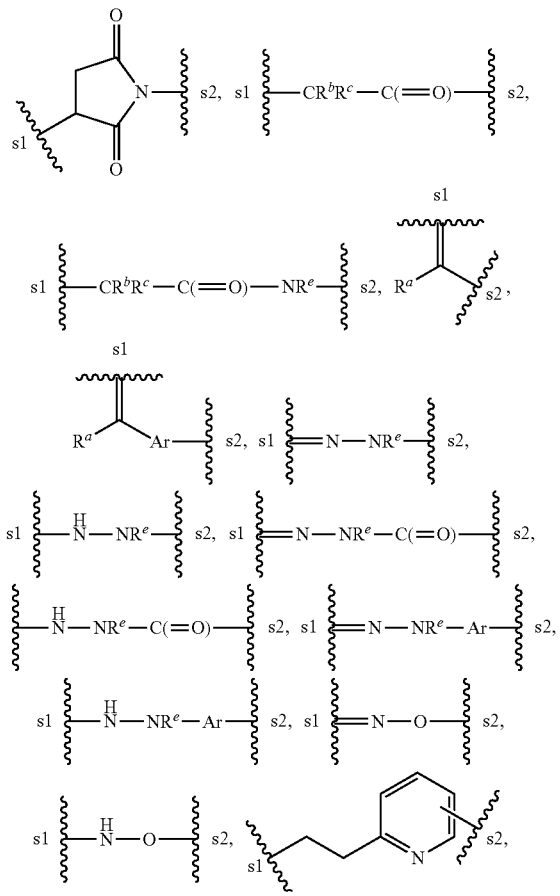

-continued

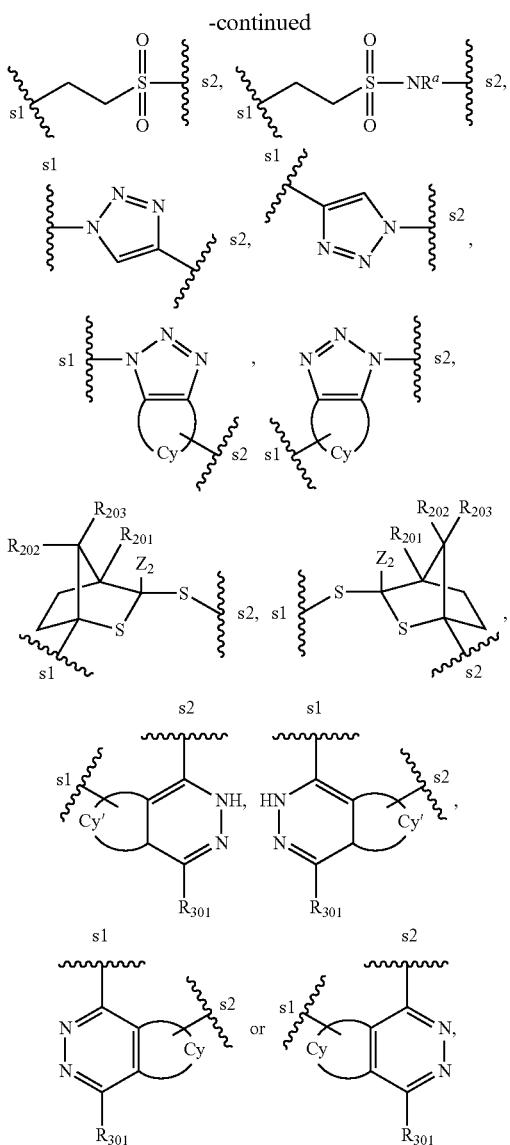

in which s1 is the site covalently linked to the CBA, s2 is the site covalently linked to the group $(CR_{10}R_{11})_q$ in Formula (III) or (III'), and Ar is an optionally substituted arylene or an optionally substituted heteroarylene; $R^a$, $R^b$, $R^c$, and $R^e$, for each occurrence, are independently H or an optionally substituted alkyl; Z is absent, $-SO_2NR_9-$, $-NR_9SO_2-$, $-C(=O)-NR_9-$, $-NR_9-C(=O)-$, $-C(=O)-O-$, $-O-C(=O)-$, $-C(=O)-NR_9-(CH_2CH_2O)_p-$, $-NR_9-C(=O)-(CH_2CH_2O)_p-$, $-(OCH_2CH_2)_p-C(=O)NR_9-$, or $-(OCH_2CH_2)_p-NR_9-C(=O)-$; p is an integer from 1 to 1000 (preferably 1 to 24, 2 to 8, 2 to 4, or 2, 4, 8, or 24); $Z_1$ in formula (III') is absent, $-SO_2NR_9-$, $-NR_9SO_2-$, $-C(=O)-NR_9-$, $-NR_9-C(=O)-$, $-(CH_2CH_2)_{p'}$, $-NR_9-C(=O)-$, $-C(=O)-NR_9(CH_2CH_2)_{p'}$, $-(CH_2CH_2)_{p'}-C(=O)NR_9-$, $-NR_9C(=O)(CH_2CH_2)_{p'}-$, $-C(=O)-O-$, or $-O-C(=O)-$; p' is an integer from 1 to 10 (preferably 1 to 5, more preferably 2, 3 or 4); Q is H, a charged substituent or an ionizable group; $R_9$, $R_{10}$, $R_{11}$, $R_{12}$, and $R_{13}$, for each occurrence, are independently H or an optionally substituted alkyl; q and r, for each occurrence, are independently an integer between 0 and 10; Cy is the non-alkyne residue of an optionally substituted cycloalkyne or an optionally substituted heterocycloalkyne (see below in the fourth embodiment); $R_{201}$, $R_{202}$ and $R_{203}$ each are independently H or an optionally substituted alkyl (preferably, $R_{201}$, $R_{202}$ and $R_{203}$ are all H; or $R_{201}$ is $CH_3$ and $R_{202}$ and $R_{203}$ are both H); $Z_2$ is pyridyl or

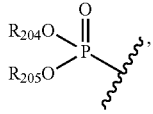

wherein $R_{204}$ and $R_{205}$ are each independently optionally substituted alkyl (preferably, $R_{204}$ and $R_{205}$ are both methyl or ethyl) and Cy' is the non-alkene residue of an optionally substituted strained cycloalkene or an optionally substituted strained heterocycloalkene (see below in the fourth embodiment); and $R_{301}$ is H or optionally substituted alkyl (preferably $R_{301}$ is H) The remainder of the variables is as defined in the first embodiment.

A third embodiment of the invention features a cytotoxic compound represented by the following formula, or a salt (e.g., a pharmaceutically acceptable salt) thereof:

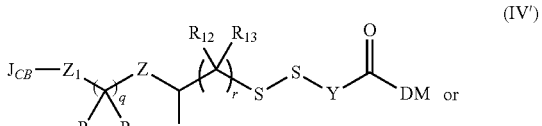

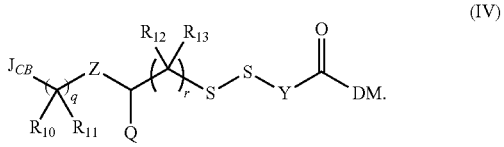

In Formula (IV) or (IV') above, $J_{CB}$ is maleimide

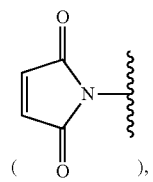

$X'-CR^bR^c-C(=O)-$, $X'-CR^bR^c-C(=O)-NR^e-$, $R^a-C(=O)-$, $R^a-C(=O)-Ar-$, $NH_2-NR^e-$, $NH_2-NR^e-C(=O)-$, $NH_2-NR^e-Ar-$, $NH_2-O-$,

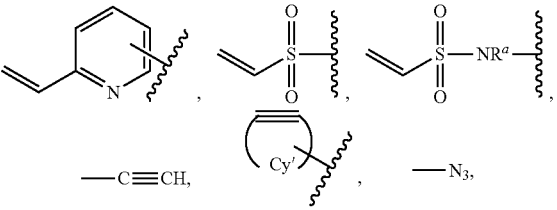

-continued

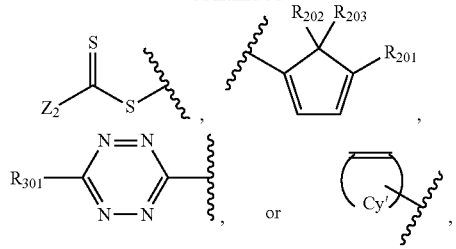

in which X' is a halogen;

is an optionally substituted cycloalkyne or an optionally substituted heterocycloalkyne,

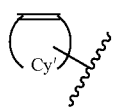

is an optionally substituted strained cycloalkene or an optionally substituted strained heterocycloalkene, and the remainder of the variables is as defined in the second embodiment above. Preferably,

is an optionally substituted cycloalkyne or an optionally substituted heterocycloalkyne that can readily react with an azide to form a triazole through copper free click chemistry or can readily react with a tetrazine (see, for example, *J. Am. Chem. Soc.* (2012) 134:9199-9208; WO 2011/136645; US 2009/0068738, Lang K. et al. *J. Am. Chem. Soc.* (2012)134: 10317-10320, the entire teaching of these references are incorporated herein by its entirety). More preferably,

is cyclooctyne. In another preferred embodiment,

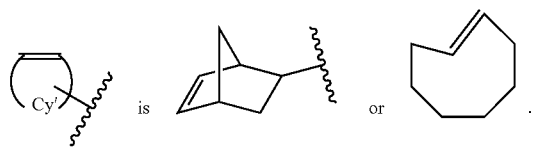

A fourth embodiment of the invention features a linker compound represented by the following formula, or a salt (e.g., a pharmaceutically acceptable salt) thereof:

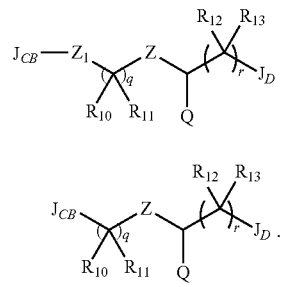

In Formula (V) or (V'), $J_D$ is SH, $SSR^d$ or —S—C(=O)$R^g$, wherein $R^d$ is phenyl, nitrophenyl, dinitrophenyl, carboxynitrophenyl, pyridyl or nitropyridyl; and $R^g$ is alkyl; and the remainder of the variables is as defined in the third embodiment above.

A fifth embodiment of the invention features a modified cell-binding agent represented by the following formula, or a salt (e.g., a pharmaceutically acceptable salt) thereof:

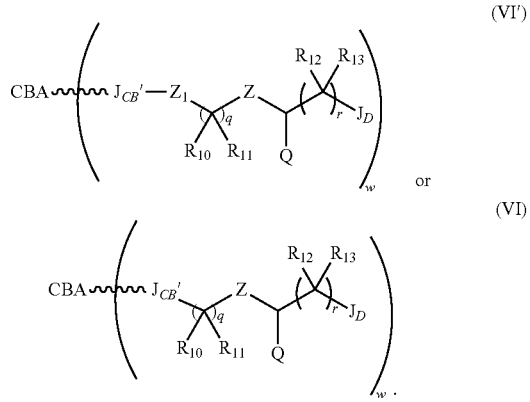

In Formula (VI) or (VI'), $J_D$ is as defined in the fourth embodiment and the remainder of the variables is as defined in the second embodiment above.

In an alternative embodiment, in Formula (III'), (III), (IV'), (IV), (V'), (V), (VI') or (VI), Ar is phenylene. In another alternative embodiment, q and r, in Formula (III), (III'), (IV'), (IV), (V'), (V), (VI') or (VI), for each occurrence, are independently an integer between 2 and 5. In yet another alternative embodiment, in Formula (III'), (III), (IV'), (IV), (V'), (V), (VI') or (VI), Ar is phenylene, and q and r, for each occurrence, are independently an integer between 2 and 5. The remainder of the variables in each of the alternative embodiments above is as defined in the first, second, third, fourth or fifth embodiment.

In another alternative embodiment, in Formula (III), (IV), (V) or (VI), Z is absent, —C(=O)NR$_9$— or —NR$_9$C(=O)—. Alternatively, Z is absent. In another alternative, Z is —NR$_9$C(=O)—. In another alternative, Z is —NR$_9$—C(=O)—(CH$_2$CH$_2$O)$_p$—, or —(OCH$_2$CH$_2$)$_p$—C(=O)NR$_9$—.

Also within the scope of this invention is a composition (e.g., a pharmaceutical composition) comprising a conjugate represented by Formula (I), (III') or (III), a cytotoxic compound represented by Formula (IV') or (IV), or a salt (e.g., a pharmaceutical acceptable salt) thereof. The composition may also include a carrier (e.g., a pharmaceutically acceptable carrier). The composition can further include a second therapeutic (e.g., chemotherapeutic) agent.

The present invention also includes a method of inhibiting abnormal cell growth or treating a proliferative disorder, a destructive bone disorder, an autoimmune disorder, a graft versus host disease, a transplant rejection, an immune deficiency, an inflammatory diseases, an infectious disease, a viral disease, a fibrotic disease, a neurodegenerative disorder, pancreatitis, or a kidney disease in a mammal (e.g., human), comprising administering to said mammal a therapeutically effective amount of a conjugate represented by any one of Formula (I), (III') or (III), a cytotoxic compound represented by Formula (IV') or (IV), or a salt (e.g., a pharmaceutical acceptable salt) thereof.

In a related embodiment, the method described above further comprises administering to said mammal sequentially or consecutively a second therapeutic (e.g., chemotherapeutic) agent.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

"Alkyl" as used herein refers to a saturated linear or branched-chain monovalent hydrocarbon radical of one to twenty carbon atoms. "Monovalent" means that alkyl has one point of attachment to the remainder of the molecule. Examples of alkyl groups include, but are not limited to, methyl, ethyl, 1-propyl, 2-propyl, 1-butyl, 2-methyl-1-propyl, —CH$_2$CH(CH$_3$)$_2$, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl group has one to ten carbon atoms. More preferably, the alkyl group has one to four carbon atoms.

"Alkylene" as used herein refers to a saturated linear or branched-chain divalent hydrocarbon radical of one to twenty carbon atoms, examples of which include, but are not limited to, those having the same core structures of the alkyl groups as exemplified above. "Divalent" means that the alkylene has two points of attachment to the remainder of the molecule. Preferably, the alkylene group has one to ten carbon atoms. More preferably, the alkylene group has one to four carbon atoms.

As used herein, an integer "between" x and y includes integers x and y unless otherwise specified to the contrary. For example, "an integer between 1 and 5" can be 1, 2, 3, 4, or 5.

The terms "cyclic alkyl" and "cycloalkyl" can be used interchangeably. They refer to a monovalent saturated carbocyclic ring radical. "Monovalent" means that cycloalkyl has one point of attachment to the remainder of the molecule. The saturated carbocyclic ring can be monocyclic or bicyclic (fused, bridged, or spiro bicyclic). Preferably, the cycloalkyl is 3 to 7 membered monocyclic ring radical. Bicyclic cycloalkyl having 7 to 12 atoms can be arranged, for example, as a bicyclo[4,5], [5,5], [5,6], or [6,6] system, and bicyclic cycloalkyl having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Bicyclic cycloalkyl also include a spiro cycloalkyl with rings connected through just one atom. Examples of monocyclic cycloalkyl groups include, but are not limited to, cyclopropyl, cyclobutyl, cyclopentyl, cyclohexyl, cycloheptyl, cyclooctyl, cyclononyl, cyclodecyl, cycloundecyl, cyclododecyl, and the like. More preferably, the cycloalkyl is cyclohexyl.

"Cycloalkylene" as used herein refers to a divalent saturated carbocyclic ring radical having 3 to 12 carbon atoms as a monocyclic ring, or 7 to 12 carbon atoms as a bicyclic ring. "Divalent" means that the cycloalkylene has two points of attachment to the remainder of the molecule. Preferably, the cycloalkylene is a 3- to 7-membered monocyclic. Examples of cyclic alkylene groups include, but not limited to, those having the same core structures of the cylcolakyl groups as exemplified above. More preferably, the cycloalkylene group is cyclohexylene.

"Cycloalkyne" as used herein refers carbocyclic ring having one or more triple bonds. It can be monocyclic, bicyclic or tricyclic; bicyclic and tricyclic can be bridged or fused. The carbocyclic ring optionally contains one or more double bonds and/or is optionally fused with one or more aromatic (e.g., phenyl ring) or heteroaromatic rings. Examples of cycloalkyne include, but are not limited to, those described in *J. Am. Chem. Soc.* (2012) 134:9199-9208; WO 2011/136645, US 2009/0068738, Lang K. et al. *J. Am. Chem. Soc.* (2012) 134:10317-10320, for example, cyclooctyne, monofluorocyclooctyne, difluorooctyne, DIFO, DIFO$_2$, DIFO$_3$, bicylo[6.1.0]non-4-yne, benzocyclooctyne, difluorobenzocyclooctyne, dibenzocyclooctyne, DIBO, and those described in Debets, M. F. et al., *Acc. Chem. Res.* (2011) 44(9):805-815; and Gold B. et al., *J. Am. Chem. Soc.* (2013) 135(4):1558-1569. Preferably, cycloalkyne is cyclooctyne.

"Heterocycloalkyne" as used herein refers to a heterocyclic ring having one or more triple bonds. Examples of heterocycloalkyne include, but are not limited to, dibenzoazacyclooctyne (DIBAC), biarylazacyclooctynone (BARAC), thiacyclooctyne, thiabenzocyclooctyne, thiacycloheptyne and tetramethylthiacycloheptyne.

"Strained cycloalkene" as used herein refers to carbocyclic ring having one or more double bonds, in which at least one of the double bonds is in the trans configuration and forced by structural constraints have bond angles other than the typical 120° angle of non-strained alkenes. The strained cycloalkenes are more reactive than non-strained alkenes. Examples of strained cycloalkene include, but are not limited to, trans-cyclooctene, norbornene and other cycloalkenes described in Debets, M. F. et al. *Acc. Chem. Res.*, (2011) 44(9):805-815.

"Strained heterocycloalkene" as used herein refers to a heterocyclic ring having one or more double bonds, in which at least one of the double bonds is in the trans configuration and forced by structural constraints have bond angles other than the typical 120° angle of non-strained heterocycloalkenes. The strained heterocycloalkenes are more reactive than non-strained heterocycloalkenes.

The term "aryl group" means an aromatic hydrocarbon ring system having six to fourteen carbon ring atoms. The term "aryl" may be used interchangeably with the terms "aryl ring" "aromatic ring," "aryl group" and "aromatic group". "Aryl group" also includes an aromatic hydrocarbon ring system fused to a non-aromatic carbocyclic ring system, such as a cycloalkyl group. Examples includes phenyl, naphthyl, anthracenyl, 1,2-dihydronaphthyl, 1,2,3,4-tetrahydronaphthyl, fluorenyl, indanyl, indenyl and the like. An aryl group is monovalent, i.e., has one point of attachment to the remainder of the molecule. A "substituted aryl group" is substituted at any one or more substitutable ring atom, which is a ring carbon atom bonded to a hydrogen."

"Arylene" as used herein refers to a divalent aryl group, i.e., an aryl group having two points of attachment to the remainder of the molecule. "Divalent" means that the arylene has two points of attachment to the remainder of the molecule. Both aryl and arylene groups are sometime represented herein by "Ar." Arylene is preferably phenylene.

"Heteroaryl" (used interchangeably with "heteroaromatic," "heteroaryl ring," "heteroaryl group," "heteroaromatic ring," and "heteroaromatic group") refers to aromatic ring systems having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings (e.g., bicyclic) in which a monocyclic heteroaromatic ring is fused to one or more other aromatic or heteroaromatic rings. As such, "5-14 membered heteroaryl" includes monocyclic, bicyclic or tricyclic ring systems. Heteroaryls are monovalent, meaning that there is one point of attachment to the remainder of the molecule.

"Monocyclic 5-6 membered heteroaryl" means a monocyclic aromatic ring system having five or six ring atoms selected from carbon and at least one (typically 1 to 3, more typically 1 or 2) heteroatoms (e.g., oxygen, nitrogen or sulfur). Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

"Heteroarylene" as used herein refers to a divalent heteroaryl, i.e., a heteroaryl with two points of attachment to the remainder of the molecule.

The terms "heterocycle," "heterocyclyl," heterocyclic and "heterocyclic ring" are used interchangeably herein and refer to a saturated or unsaturated non-aromatic 3-12 membered ring radical optionally containing one or more double bonds. It can be monocyclic, bicyclic, or tricyclic; bicyclic and tricyclic can be bridged or fused. The heterocycle contains 1 to 4 heteroatoms, which may be the same or different, selected from N, O or S. The heterocycle optionally contains one or more double bonds and/or is optionally fused with one or more aromatic (e.g., phenyl ring) or heteroaromatic rings. "3-7 membered monocyclic heterocycle" means a radical having from 3-7 atoms (including 1-3 heteroatoms) arranged in a monocyclic ring. The term "heterocycle" is intended to include all the possible isomeric forms. A heterocycle may be a monocycle having 3 to 7 ring members (e.g., 2 to 6 carbon atoms and 1 to 4 heteroatoms selected from N, O, P, and S) or a bicycle having 7 to 10 ring members (e.g., 4 to 9 carbon atoms and 1 to 6 heteroatoms selected from N, O, P, and S), for example: a bicyclo[4,5], [5,5], [5,6], or [6,6] system. Heterocycles are described in Paquette, Leo A., *Principles of Modern Heterocyclic Chemistry* (W. A. Benjamin, N.Y., 1968), particularly Chapters 1, 3, 4, 6, 7, and 9; *The Chemistry of Heterocyclic Compounds, A series of Monographs* (John Wiley & Sons, New York, 1950 to present), in particular Volumes 13, 14, 16, 19, and 28; and *J. Am. Chem. Soc.* (1960) 82:5566.

Examples of heterocyclic rings include, but are not limited to, aziridinyl, pyrrolidinyl, tetrahydrofuranyl, dihydrofuranyl, tetrahydrothienyl, tetrahydropyranyl, dihydropyranyl, tetrahydrothiopyranyl, tetrahydropyrrolyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, isoindolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The heterocycle, heteroaryl, or heteroarylene groups may be carbon (carbon-linked) or nitrogen (nitrogen-linked) attached where such is possible. By way of example and not limitation, carbon bonded heterocycle, heteroaryl or heroarylene groups are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycle, heteroaryl, or heteroarylene groups are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole or isoindoline, position 4 of a morpholine, and position 9 of a carbazole, or O-carboline.

The heteroatoms present in heteroaryl, heteroarylene, or heterocyclyl can include the oxidized forms such as NO, SO, and $SO_2$.

"Halogen" refers to F, Cl, Br or I.

If a group is described as being "optionally substituted," the group may be either (1) not substituted, or (2) substituted. If a carbon of a group is described as being optionally substituted with one or more of a list of substituents, one or more of the hydrogen atoms on the carbon (to the extent there are any) may separately and/or together be replaced with an independently selected optional substituent.

Suitable substituents for an alkyl, alkenyl, alkynyl, cycloalkyl, aryl, heteroaryl, heterocycle, alkylene, alkenylene, alkynylene, cycloalkene, heterocycloalkene, cycloalkyne, heterocycloalkyne, cycloalkylene arylene, and heterarylene are those which do not significantly adversely affect the biological activity of the conjugate. Unless otherwise specified, exemplary substituents for these groups include linear, branched or cyclic alkyl, alkenyl or alkynyl having from 1 to 10 carbon atoms, aryl, heteroaryl, heterocyclyl, halogen, guanidinium [—NH(C=NH)NH$_2$], —OR$_{100}$, NR$_{101}$R$_{102}$, —NO$_2$, —NR$_{101}$COR$_{102}$, —SR$_{100}$, a sulfoxide represented by —SOR$_{101}$, a sulfone represented by —SO$_2$R$_{101}$, a sulfonate —SO$_3$M, a sulfate —OSO$_3$M, a sulfonamide represented by —SO$_2$NR$_{101}$R$_{102}$, cyano, an azido, —COR$_{101}$, OCOR$_{101}$, —OCONR$_{101}$R$_{102}$ and a polyethylene glycol unit (—OCH$_2$CH$_2$)$_n$R$_{101}$ wherein M is H or a cation (such as Na$^+$ or K$^+$); R$_{101}$, R$_{102}$ and R$_{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$_{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$_{104}$ is H or a linear or branched alkyl having 1 to 4 carbon atoms, wherein the alkyl, alkenyl, alkynyl, aryl, heteroaryl and heterocyyl in the groups represented by R$_{100}$, R$_{101}$, R$_{102}$, R$_{103}$ and R$_{104}$ are optionally substituted with one or more (e.g., 2, 3, 4, 5, 6 or more) substituents independently selected from halogen, —OH, —CN, —NO$_2$, and unsubstituted linear or branched alkyl having 1 to 4 carbon atoms. Preferably, the substituent for the optionally substituted alkyl, alkylene, cycloalkylene, arylene, and heteroarylene described above is selected from the group consisting of halogen, —CN, —NR$_{101}$R$_{102}$, —CF$_3$, —OR$_{100}$, aryl, heteroaryl, heterocyclyl, —SR$_{101}$, —SOR$_{101}$, —SO$_2$R$_{101}$, and —SO$_3$M. Alternatively, the suitable substituent is selected from the group consisting of -halogen, —OH, —NO$_2$, —CN, C$_{1-4}$ alkyl, —OR$_{100}$, NR$_{101}$R$_{102}$, —NR$_{101}$COR$_{102}$, —SR$_{100}$, —SO$_2$R$_{101}$, —SO$_2$NR$_{101}$R$_{102}$, —COR$_{101}$, —OCOR$_{101}$, and —OCONR$_{101}$R$_{102}$, wherein R$_{100}$, R$_{101}$, and R$_{102}$ are each independently —H or C$_{1-4}$ alkyl.

"Alkenyl" as used herein refers to aliphatic linear or branched-chain monovalent hydrocarbon radical of two to twenty carbon atoms with at least one carbon-carbon double bond, wherein the alkenyl radical includes radicals having "cis" and "trans" orientations, or by an alternative nomenclature, "E" and "Z" orientations. "Monovalent" means that alkenyl has one point of attachment to the remainder of the molecule. Examples include, but are not limited to, ethylenyl or vinyl (—CH=CH$_2$), allyl (—CH$_2$CH=CH$_2$), and the like. Preferably, the alkenyl has two to ten carbon atoms, also referred to as "C$_{2-10}$ alkenyl." More preferably, the alkenyl has two to four carbon atoms, also referred to as "C$_{24}$ alkenyl."

"Alkynyl" as used herein refers to aliphatic linear or branched-chain monovalent hydrocarbon radical of two to twenty carbon atoms with at least one carbon-carbon triple bond. "Monovalent" means that alkynyl has one point of attachment to the remainder of the molecule. Examples include, but are not limited to ethynyl, propynyl, 1-butynyl, 2-butynyl, 1-pentynyl, 2-pentynyl, 3-pentynyl, hexynyl, and the like. Preferably, the alkynyl has two to ten carbon atoms, also referred to as "C$_{2-10}$ alkynyl." More preferably, the alkynyl has two to four carbon atoms, also referred to as "C$_{24}$ alkynyl."

The term "ionizable group" refers to a functional group that can be converted to a charged group by protonation with an acid or deprotonation with a base. Examples of the ionizable groups include —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'CO$_2$H, —NR$_{11}$R$_{12}$, or —Z'—NR$_{11}$R$_{12}$, R$_{11}$ and R$_{12}$, for each occurrence, are independently H or an optionally substituted alkyl; and Z' includes an optionally substituted alkylene, an optionally substituted cycloalkylene or an optionally substituted phenylene. In certain embodiments, Z' is alkylene.

The term "charged substituent" refers to a substituent that is either positively or negatively charged. The charge in such a substituent is not removable by treatment with a base or an acid and thus permanent. Examples of the charged substituents include, but not limited to, —N$^+$R$_{13}$R$_{14}$R$_{15}$ and —Z'—N$^+$R$_{13}$R$_{14}$R$_{15}$, in which R$_{13}$ to R$_{15}$ are each independently an optionally substituted alkyl; and Z' includes an optionally substituted alkylene, an optionally substituted cycloalkylene or an optionally substituted phenylene. In certain embodiments, Z' is alkylene.

Charged substituents may contain a counterion. For positive charged substituents, the counterion is negative and can be represented by "X$^-$," e.g., as —N$^+$R$_{13}$R$_{14}$R$_{15}$X$^-$ and —Z'—N$^+$R$_{13}$R$_{14}$R$_{15}$X$^-$. The counter ions for the positively charged substituents are anions (preferably pharmaceutically acceptable anions), which include, but are not limited to, acetate, benzenesulfonate, benzoate, bicarbonate, bitartrate, bromide, calcium edetate, camsylate, carbonate, chloride, bromide, citrate, dihydrochloride, edetate, edisylate, estolate, esylate, fumarate, glyceptate, gluconate, glutamate, glycollylarsanilate, hexylresorcinate, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide. Preferably, the counter ions for the positively charged substituents are chloride, bromide, sulfate, and phosphate.

The counter ions for the negatively charged substituents include, but are not limited to, an alkali metal ion (e.g., sodium and potassium), an alkaline earth metal ion (e.g., calcium and magnesium), aluminum ion, ammonium, protonated trialkyl amines (e.g., trimethylamine and triethylamine), a tetraalkyl ammonium (e.g., tetra methyl ammonium, and tetrabutyl ammonium), and a protonated heteroaromatic group (e.g., pyridine, pyrimidine, triazines, tetrazines). Preferably, the counter ions for the negatively charged substituents are sodium, potassium, lithium, protonated triethyl amine, protonated pyridiene. Most preferably, the counter ions for the negatively charged substituents are sodium and potassium. The counter ions for both the negatively and positively charged substituents may be removed or replaced in subsequent purification steps.

The term "reactive ester" as used herein refers to an ester group having a leaving group that is readily displaced by an amine group. Examples of a reactive ester, include, but are not limited to, N-hydroxysuccinimide ester, N-hydroxysulfosuccinimide ester, nitrophenyl (e.g., 2 or 4-nitrophenyl) ester, dinitrophenyl (e.g., 2,4-dinitrophenyl) ester, sulfotetrafluorophenyl (e.g., 4-sulfo-2,3,5,6-tetrafluorophenyl)ester and pentafluorophenyl ester.

As used herein, the terms "DARPin" and "(designed) ankyrin repeat protein" are used interchangeably to refer to certain genetically engineered antibody mimetic proteins typically exhibiting preferential (sometimes specific) target binding. The target may be protein, carbohydrate, or other chemical entities, and the binding affinity can be quite high. The DARPins may be derived from natural ankyrin repeat-containing proteins, and preferably consist of at least three, usually four or five ankyrin repeat motifs (typically about 33 residues in each ankyrin repeat motif) of these proteins. In certain embodiments, a DARPin contains about four- or five-repeats, and may have a molecular mass of about 14 or 18 kDa, respectively. Libraries of DARPins with randomized potential target interaction residues with diversities of over $10^{12}$ variants can be generated at the DNA level, for use in selecting DARPins that bind desired targets (e.g., acting as receptor agonists or antagonists, inverse agonists, enzyme inhibitors, or simple target protein binders) with picomolar affinity and specificity, using a variety of technologies such as ribosome display or signal recognition particle (SRP) phage display. See, for example, U.S. Patent Publication Nos. 2004/0132028, 2009/0082274, 2011/0118146, and 2011/0224100, WO 02/20565 and WO 06/083275 (the entire teachings of which are incorporated herein by reference), and also see C. Zahnd et al. (2010) *Cancer Res.*, 70:1595-1605; Zahnd et al. (2006) *J. Biol. Chem.*, 281(46): 35167-35175; and Binz, H. K., Amstutz, P. & Pluckthun, A. (2005) *Nature Biotechnology*, 23:1257-1268 (all incorporated herein by reference). Also see U.S. Patent Publication No. 2007/0238667; U.S. Pat. No. 7,101,675; WO 2007/147213; and WO 2007/062466 (the entire teachings of which are incorporated herein by reference), for the related ankyrin-like repeats protein or synthetic peptide. As used herein, "AVIBODY™" cell binding agents (or "AVIBODY CBA" in short) includes a family of proteins as cell binding agents that specifically bind desired targets. As is well known, antibodies bind such desired targets through "Target Binding Regions" (TBRs) or Fv domains. AVIBODY™ CBA typically contains two, three, or four TBRs more commonly known as Dia-, Tria- and Tetra-bodies. These TBRs/Fv domains are linked together by fusing the Fv V-domains together in a "head to tail" orientation, forming stable, specific, and highly customizable multimeric antibody-like proteins as AVIBODY™ CBA. See, for example, U.S. Publication Nos. 2008/0152586 and 2012/0171115 for details, the entire teachings of which are incorporated herein by reference.

The term "cell binding agent" as used herein refers to a compound that can bind a cell (e.g., on a cell-surface ligand) or bind a ligand associated with or proximate to the cell, either in a specific or non-specific manner. In certain embodiments, binding to the cell or a ligand on or near the cell is specific. The cell-binding agent may be of any kind presently known, or that become known and includes peptides and non-peptides.

In certain embodiments, the cell-binding agents are proteins or polypeptides, or compounds comprising proteins or polypeptides, including both antibody and non-antibody proteins or polypeptides. Preferably, the cell-binding agents (e.g., proteins or polypeptides) comprise one or more Cys residues. The side chain —SH group of the Cys residues may be intact, or may be in a disulfide bond that can be reduced. Preferably, reduction of the disulfide bond(s) does not significantly negatively impact the cell-binding function of the proteins or polypeptides (e.g., in the case of antibody or antigen-binding portion thereof, reduction of the disulfide bonds does not substantially increase the dissociation of light chains/heavy chains). Alternatively or in addition, the cell-binding agents (e.g., proteins or polypeptides) comprise one or more amino acids that are modified to contain a reactive functional group that can react with the linkers (e.g., Formula (V') or (V)) or cytotoxic compounds (e.g., Formula (IV') or (IV)) of the invention. For example, the reactive functional group is —SH, —C(=O)—, —NHNH$_2$, —N$_3$, -alkyne, tetrazine, strained cycloalkene or strained heterocycloalkene, dithioester, or diene (see, for example, Vu Hong et al., *Bioconjugate Chem*. (2010) 21(10):1912-1916; Glassner, M. et al., *J. Am. Chem. Soc*. (2012) 134:7274-7277; Hansell, C. F. et al. *J. Am. Chem. Soc.* (2011) 133:13828-13831; Neal K. Devaraj, Synlett (2012) 23(15): 2147-2152; Chenoweth, K. et al., *Organic & Biomolecular Chemistry* (2009) 7(24):5255; Jewett, J. C. et al., *J. Am. Chem. Soc.* (2010) 132(11):3688-3690; Seitchik, J. L. et al., *J. Am. Chem. Soc.* (2012) 134(6):2898-2901; and Sletten E. M. et al., *Angew Chem. Int. Ed. Engl.* (2009) 48(38):6974-6998). The reactive functional group can be introduced into the cell-binding agent through any chemical or enzymatic method known in the art. See, for example, Davis L. K. et al., *J Am Chem Soc.* (2012) 134:10317-10320; Boeggeman E et al., *Bioconjug Chem.* (2009 Jun. 20) (6):1228-1236; Stan, A C, et al., *Cancer Res.* (1999 Jan. 1) 59(1):115-121; Mahal, L. K. et al., *Science* (1997) 276:1125-1128; Saxon, E., and Bertozzi, C. R. *Science* (2000) 287:2007-2010; Hang, H. C. et al. *Proc. Natl. Acad. Sci. USA* (2003) 100:14846-14851; Vocadlo, D. J. et al., *Proc. Natl. Acad. Sci. USA,* (2003) 100:9116-9121; Prescher, J. A. et al., *Nature* (2004) 430:873-877; Dube, D. H. et al. (2006) *Proc. Natl. Acad. Sci. USA* 103:4819-4824; Jeger S, et al., *Angew Chem Int Ed Engl.* (2010 Dec. 17) 49(51):9995-9997; and Lang K. et al., *J. Am. Chem. Soc.* (2012) 134:10317-10320.

Cell-binding agent can also be peptides derived from phage display (see, for example, Wang et al., *Proc. Natl. Acad. Sci. USA* (2011) 108(17), 6909-6914) or peptide library techniques (see, for example, Dane et al., *Mol. Cancer. Ther.* (2009) 8(5):1312-1318).

In one embodiment, one or more reactive functional groups that are capable of reacting with the linkers (Formula (V') or (V)) or the cytotoxic compounds (Formula (IV') or (IV)) of the present invention can be introduced into the cell-binding agent by any methods known in the art. For example, a terminal amine group on the cell-binding agent can be converted to a carbonyl group through transamination reaction (see, for example, US2010/0099649; *Angew. Chem. Int.* (2006) Ed., 45 (32):5307; *Chem. Biol.*, 2(4), 247, 2007; *J. Am. Chem. Soc.* (2008) 130(35):11762). Alternatively, the cell-binding agent can be engineered to include one or more free cysteine residues (i.e., cysteine residues having a free —SH group that can react with the linkers or the cytotoxic compounds of the present invention) according to any methods known in the art (see, for example, U.S. Pat. No. 7,521,541). In another alternative, thiol groups (—SH) can be generated by controlled reduction of interchain disulfides of antibodies, followed by treatment with a cytotoxic agent bearing a maleimido group, as described in U.S. Pat. Nos. 7,659,241, 8,309,300; 7,855,275; 7,723,485 and 7,521,541. For example, partial or complete reduction of interchain disulfides followed by conjugation with a cytotoxic agent bearing a maleimido group can yield a conjugate with 2, 3, 4, 5, 6, 7 or 8 cytotoxic agent molecules covalently linked to each antibody molecule. Alternatively, conjugates having 2, 3, 4, 5, 6, particularly 4 or 6, cytotoxic agent molecules covalently attached to each antibody molecule can be prepared by complete reduction of interchain disulfide of the antibody followed by partial re-oxidation and then conjugation with cytotoxic agent. In another alternative, these conjugates can be prepared by partial or complete reduction of interchain disulfides of the antibody followed by conjugation with cytotoxic agent and then partial re-oxidation. Thiol groups can also be introduced into the cell-binding agent (e.g., antibodies) by reaction with a crosslinking agent such as 2-iminothiolane (see for example Goff and Carroll, *Bioconjugate Chem.* (1990) 1(6):381-386) followed by reaction with a cytotoxic agent bearing a maleimido group (e.g., compounds of Formula (IV') or (IV)) to provide a conjugate. All these methods for introducing reactive functional groups are applicable for cell-binding agents that are not antibodies, which, for example, include centyrin, Darpin, Avibody, adnectin or antibody fragment, such as minibodies, diabodies, tribodies, tetrabodies, nanobodies, probodies, domain bodies or unibodies.

In one embodiment, when the cell-binding agent is a centyrin, one or more reactive functional groups (e.g., a cysteine having a free thiol group) can be introduced according to methods described in US2010/0255056, US2010/0216708 and US2011/0274623.

In another embodiment, the cell-binding agent is a Darpin and it can be prepared according to methods described in US Publication Nos. 2004/0132028, 2009/0082274, 2011/0118146, and 2011/0224100, WO 02/20565 and WO 06/083275. Preferably, Darpin comprises one or more cysteine residues at specific positions that do not interfere with antigen binding. Such cysteine residue can react with the linkers (e.g., Formula (V') or (V)) or the cytotoxic compounds (e.g., Formula (IV') or (IV)) of the present invention.

In yet another embodiment, Avibodies having one or more cysteine residues can be prepared according to methods described in US 2008/0139791 and US 2012/0171115.

The Cys side chain —SH groups or the other reactive functional groups described above may be covalently linked to the linkers (e.g., linkers of Formula (V') or (V)), which are in turn linked to the cytotoxic compounds, thus conjugating the cell-binding agents to the cytotoxic compounds to yield the conjugates of the invention (e.g., conjugates of Formula (III') or (III)). Alternatively, the Cys side chain —SH groups or the reactive functional groups may be covalently linked to the cytotoxic compounds of the invention having linkers bound thereto (e.g., cytotoxic compounds of Formula (IV') or (IV)). Each protein-based cell-binding agents may contain multiple Cys side chain —SH groups and/or the reactive functional groups available for linking the compounds of the invention.

Examples of the cell binding agents include an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a bispecific antibody, a domain antibody, a domain antibody fragment that specifically binds to the target cell, an interferon, a lymphokine (e.g., IL-2, IL-3, IL-4, and IL-6), a hormone (e.g., insulin, thyrotropin releasing hormone, melanocyte-stimulating hormone, and a steroid hormone (e.g., androgen and estrogen)), a vitamin (e.g., folate), a growth factor (e.g., EGF, TGF-alpha, FGF, VEGF), a colony stimulating factor, a nutrient-transport molecule (e.g., transferrin; see O'Keefe et al. (1985) *J. Biol. Chem.* 260:932-937, incorporated herein by reference), a centyrin (a protein scaffold based on a consensus sequence of fibronectin type III (FN3) repeats; see U.S. Patent Publication 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., *Cancer Res.* (2010) 70:1595-1605; Zahnd et al., *J. Biol. Chem.* (2006) 281(46):35167-35175; and Binz, H. K., Amstutz, P. & Pluckthun, A., *Nature Biotechnology* (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Avibody (including diabodies, triabodies, and tetrabodies; see U.S. Publication Nos. 2008/0152586 and 2012/0171115), and other cell-binding molecules or substances.

In certain embodiments, the cell-binding agent is an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule. Alternatively, the cell-binding agent is a monoclonal antibody, a single chain monoclonal antibody, or a monoclonal antibody fragment that specifically binds to a target cell.

In certain embodiments, the cell-binding agent is a bispecific antibody, an ankyrin repeat protein, a Centyrin, or an Avibody.

"Antibody fragment" refers to Fab, Fab', and F(ab')$_2$, Fv, minibodies, diabodies, tribodies, tetrabodies, nanobodies, probodies, domain bodies, unibodies, and the like (Parham, *J. Immunol.* 131:2895-2902 (1983); Spring et al. *J. Immunol.* 113:470-478 (1974); Nisonoff et al. *Arch. Biochem. Biophys.* 89:230-244 (1960), Kim et al., *Mol, Cancer Ther.*, 7:2486-2497 (2008), Carter, *Nature Revs.*, 6:343-357 (2006), R. Kontermann & S. Dubel (2001) *Antibody Engineering*, Springer-Verlag, Heidelberg-New York).

In certain embodiments, the cell-binding agent is a minibody, a diabody, a tribody, a tetrabody, a nanobody, a probody, a domain body, or an unibody.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies.

Selection of the appropriate cell-binding agent is a matter of choice that depends upon the particular cell population that is to be targeted, but in general human monoclonal antibodies are preferred if an appropriate one is available. For example, the monoclonal antibody MY9 is a murine $IgG_1$ antibody that binds specifically to the CD33 Antigen (J. D. Griffin et al., *Leukemia Res.*, 8:521 (1984)) and can be used if the target cells express CD33 as in the disease of acute myelogenous leukemia (AML).

In one embodiment, the cell-binding agent is a resurfaced antibody, a resurfaced single chain antibody, or a resurfaced antibody fragment.

In another embodiment, the cell-binding agent is a humanized antibody, a humanized single chain antibody, or a humanized antibody fragment. In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody described in U.S. Provisional Application Nos. 61/307,797, 61/346,595, and 61/413,172 and U.S. application Ser. No. 13/033,723 (published as US 2012/0009181 A1). The teachings of all these applications are incorporated herein by reference in its entirety.

In certain embodiments, the cell-binding agent is an antigen-binding portion of a monoclonal antibody, sharing sequences critical for antigen-binding with an antibody disclosed herein, such as huMy9-6 or its related antibodies described in U.S. Pat. Nos. 7,342,110 and 7,557,189, incorporated herein by reference. These derivative antibodies may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody described herein. Sequences within these regions may contain conservative amino acid substitutions, including substitutions within the CDR regions. Preferably, there is no more than 1, 2, 3, 4, or 5 conservative substitutions. In an alternative, the derivative antibodies have a light chain region and/or a heavy chain region that is at least about 90%, 95%, 99% or 100% identical to an antibody described herein. These derivative antibodies may have substantially the same binding specificity and/or affinity to the target antigen compared to an antibody described herein. Preferably, the $K_d$ and/or $k_{off}$ values of the derivative antibodies are within 10-fold (either higher or lower), 5-fold (either higher or lower), 3-fold (either higher or lower), or 2-fold (either higher or lower) of an antibody described herein. These derivative antibodies may be fully human antibodies, or humanized antibodies, or chimeric antibodies. The derivative antibodies may be produced according to any art-recognized methods.

Specific exemplary antigens or ligands include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-135); insulin-like growth factor-I and -II; des(1-3)-IGF-I (brain IGF-I); an insulin-like growth factor binding protein; melanotransferrin; EpCAM; GD3; FLT3; PSMA; PSCA; MUC1; MUC16; STEAP; CEA; TENB2; an EphA receptor; an EphB receptor; a folate receptor; FOLR1; mesothelin; cripto; an $alpha_vbeta_6$; integrins; VEGF; VEGFR; EGFR; transferrin receptor; IRTA1; IRTA2; IRTA3; IRTA4; IRTA5; CD proteins (e.g., CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, and CD152), one or more tumor-associated antigens or cell-surface receptors (see US Publication No. 20080171040 or US Publication No. 20080305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigen s (e.g., a portion of the HIV envelope); a transport protein, a homing receptor; an addressin; a regulatory protein; an integrin (e.g., CD11a, CD11b, CD11c, CD18, an ICAM, VLA-4, and VCAM;) a tumor associated antigen (e.g., HER2, HER3 and HER4 receptor); endoglin; c-Met; c-kit; 1GF1R; PSGR; NGEP; PSMA; PSCA; TMEFF2; LGR5; B7H4; and fragments of any of the above-listed polypeptides.

For example, GM-CSF, a ligand/growth factor which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers, such as lung and head and neck. Somatostatin can be used to target neuroblastomas and other tumor types. Estrogen (or estrogen analogues) can be used to target breast cancer. Androgen (or androgen analogues) can be used to target testes.

The term "salt" as used herein refers to organic or inorganic salts of a compound of the invention. Preferably, a salt is a pharmaceutically acceptable salt. Other non-pharmaceutically acceptable salts are also included in the present invention. The salts include salts, formed by reacting a compound of the invention, which comprises a basic group, with an inorganic acid or organic acid (such as a carboxylic acid), and salts, formed by reacting a compound of the invention, which comprises an acidic group, with an inorganic base or organic base (such as an amine). Exemplary salts include those pharmaceutically acceptable salts described immediately below.

The term "pharmaceutically acceptable salt" as used herein refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention contains one or more basic moieties, desired salts (e.g., pharmaceutically acceptable salts) may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention contains one or more acidic moieties, desired salts (e.g., pharmaceutically acceptable salts) may be prepared by any suitable method, for example, treatment of the free acid with an inorganic, such as an alkali metal hydroxide or alkaline earth metal hydroxide, organic base, such as an amine (primary, secondary or tertiary), or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or precancerous cells. Examples of cancer include, but are not limited to, carcinoma, lymphoma, blastoma, sarcoma, and leukemia or lymphoid malignancies. More particular examples of such cancers include skin cancer (e.g., melanoma), Merkel cell carcinoma, squamous cell cancer (e.g., epithelial squamous cell cancer), lung cancer (e.g., small-cell lung cancer, non-small cell lung cancer, adenocarcinoma of the lung, and squamous carcinoma of the lung), cancer of the peritoneum, hepatocellular cancer, gastric or stomach cancer (e.g., gastrointestinal cancer), pancreatic cancer, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, testicular cancer, vulval cancer, thyroid cancer, hepatic carcinoma, anal carcinoma, penile carcinoma, acute leukemia, head and neck cancer, brain cancer (e.g., glioblastoma and neuroblastoma), cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin's lymphomas (Nodular sclerosis, Mixed cellularity, Lymphocyte-rich, Lymphocyte depleted or not depleted, and Nodular lymphocyte-predominant Hodgkin lymphoma), Non-Hodgkin's lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler's disease).

The term "therapeutic agent" encompasses both a biological agent such as an antibody, a peptide, a protein, an enzyme or a chemotherapeutic agent.

The term "Chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference.

Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al. (2006) *J. Nat. Cancer Inst.* 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

Chemotherapeutic agents may also include any of the generic drugs or biosimilars of the brand-name drugs referenced herein, or improvements thereof, including improved formulations, delivery means (sustained release, bioadhesive coating, targeted delivery etc.), and dosage forms.

The term "viral infection" refers to the invasion of a host organism's bodily tissues by disease-causing viruses. Examples of the viral infections include CMV infection, HIV infection and AIDS.

The term "parasite infection" refers to the invasion of a host organism's bodily tissues by disease-causing parasites. Examples of the parasite infections include giardiasis, amoebiasis, and schistosomiasis.

The phrase "pharmaceutically acceptable" indicates that the substance or composition must be compatible chemically and/or toxicologically, with the other ingredients comprising a formulation, and/or the mammal being treated therewith.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Cell Binding Agent-Drug Moiety Conjugates

The present invention provides a conjugate represented by Formula (I) as described in the first embodiment, its alternative embodiment represented by Formula (III) as described in the second embodiment, and their alternative embodiments. In addition, fourteen specific embodiments for the conjugate are further described below in this conjugate section.

In a first specific embodiment, the conjugate is represented by the following formula, or a pharmaceutically acceptable salt thereof:

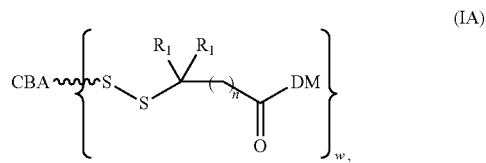

in which $R_1$ and $R_2$, for each occurrence, are independently H or an optionally substituted alkyl, and n is an integer between 0 and 10. In this first specific embodiment, the remainder of the variables is as defined in the first embodiment or each of its alternative embodiments. Preferably, the cell-binding agent does not comprise a modified lysine carrying a free thiol group (—SH), wherein the free thiol group is used to conjugate with the cytotoxic compound of the present invention. Alternatively, the cell-binding agent (CBA) in Formula (IA) is a minibody, a diabody, a tribody, a tetrabody, a nanobody, a probody, a domain body, a unibody, a bispecific antibody, an ankyrin repeat protein (e.g., a DARPin), a Centyrin, or an Avibody.

In a second specific embodiment, in Formula (IA) above, $R_1$ and $R_2$ are each methyl, n is 2, and the remainder of the variables is as defined in the first embodiment or each of its alternative embodiments.

In a third specific embodiment, in Formula (I) or (IA), DM is a drug moiety represented by the following formula:

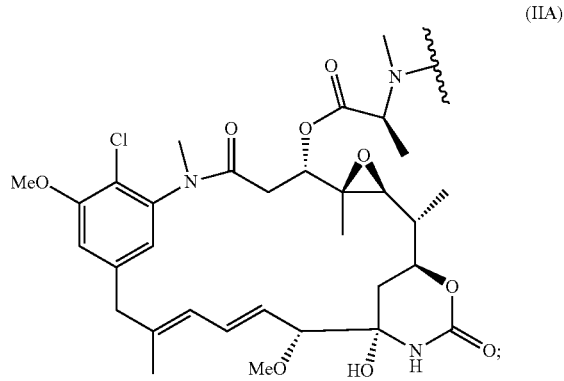 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

and the remainder of the variables is as defined in the first embodiment, or each of its alternative embodiments, or the first or second specific embodiment above.

In a fourth specific embodiment, in Formula (III') or (III), the conjugate is represented by the following formula, or a pharmaceutically acceptable salt thereof:

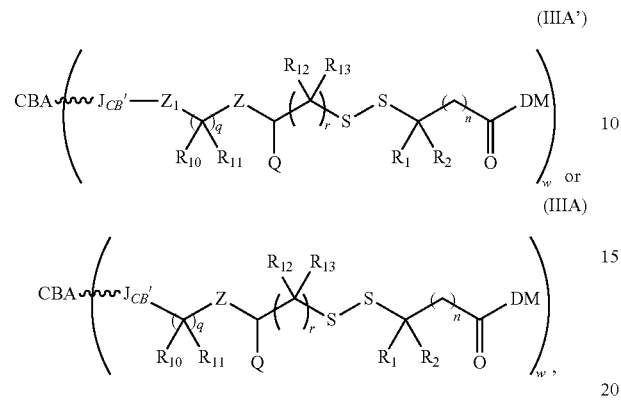

in which $R_1$ and $R_2$, for each occurrence, are independently H or an optionally substituted alkyl, n is an integer between 0 and 10, and the remainder of the variables is as defined in the second embodiment or each of its alternative embodiments. Preferably, $R_1$ and $R_2$ are both methyl; and n is 2.

In a fifth specific embodiment, in Formula (III'), (III), (IIIA') or (IIIA), Q is i) H; ii) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'13 CO$_2$H, —NR$_{11}$R$_{12}$, or —Z'—NR$_{11}$R$_{12}$, or a pharmaceutically acceptable salt thereof; or, iii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; $R_{14}$ to $R_{16}$ are each independently an optionally substituted alkyl; and X$^-$ is a pharmaceutically acceptable anion. In this fifth specific embodiment, the remainder of the variables is as defined in the second embodiment, or each of its alternative embodiments, or the fourth specific embodiment above.

In a sixth specific embodiment, variable Z' set forth in the preceding paragraph immediately above is alkylene, and the remainder of the variables is as defined in the second embodiment, or each of its alternative embodiments, or the fourth or fifth specific embodiment above.

In a seventh specific embodiment, in Formula (III'), (III), (IIIA') or (IIIA), J$_{CB'}$ is

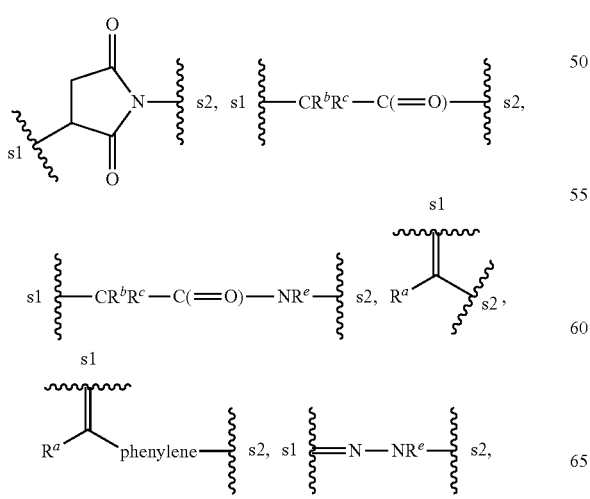

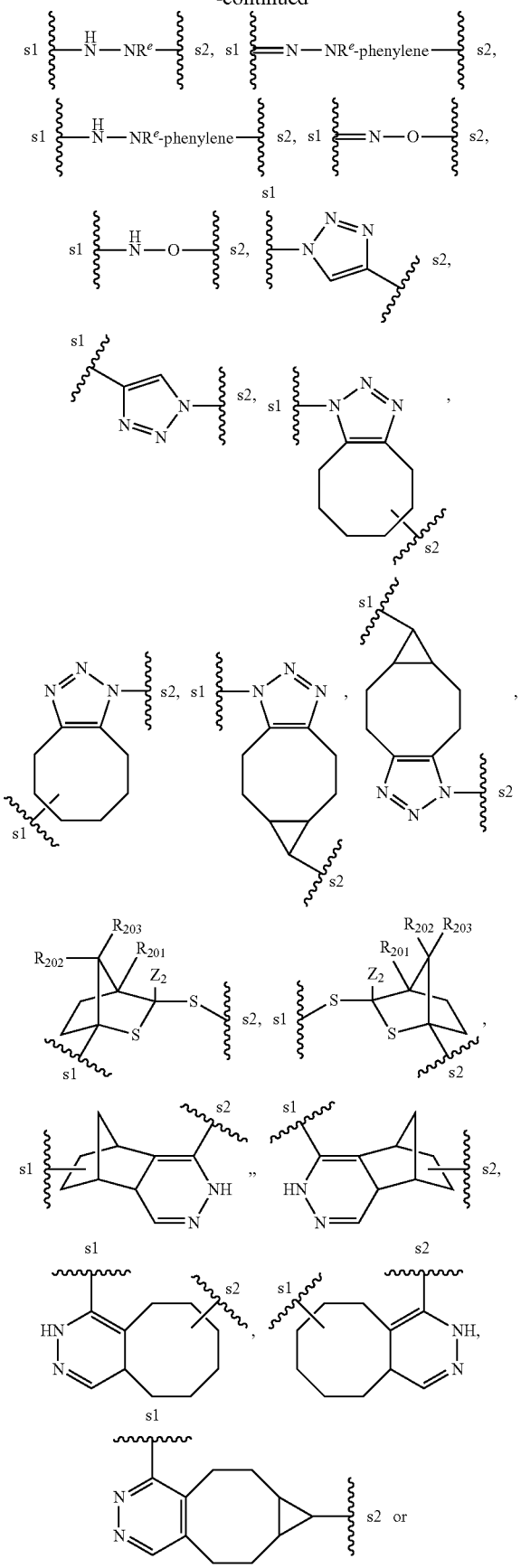

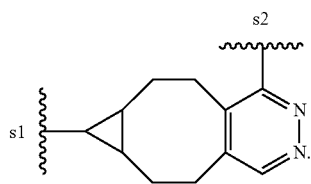

In this seventh specific embodiment, the remainder of the variables is as defined in the second embodiment, or each of its alternative embodiments, or the fourth, fifth, or sixth specific embodiment above.

In an eighth specific embodiment, in Formula (III'), (III), (IIIA') or (IIIA), $J_{CB'}$ is

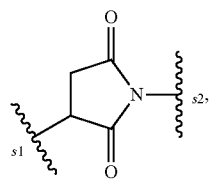 [SMILES: *C1CC(=O)N(*)C1=O]

and the remainder of the variables is as defined in the second embodiment, or each of its alternative embodiments, or the fourth, fifth, or sixth specific embodiment above.

In a ninth specific embodiment, in Formula (III'), (III), (MA') or (IIIA), Z is —C(=O)—NR$_9$— or —NR$_9$—C(=O)—, and the remainder of the variables is as defined in the second embodiment, or each of its alternative embodiments, or the fourth, fifth, sixth, seventh, or eighth specific embodiment.

In a tenth specific embodiment, in Formula (III'), (III), (MA') or (IIIA), $R^a$, $R^b$, $R^c$, and $R^e$ are each H; Z' is an optionally substituted alkylene (preferably unsubstituted alkylene); $R_9$ is H; and the remainder of the variables is as defined in the second embodiment, or each of its alternative embodiments, or the fourth, fifth, seventh, eighth, or ninth specific embodiment above.

In an eleventh specific embodiment, in Formula (III'), (III), (MA') or (IIIA), Q is H, or —SO$_3$H or a pharmaceutically acceptable salt thereof; and the remainder of the variables is as defined in the second embodiment, or each of its alternative embodiments, or the fourth, fifth, sixth, seventh, eighth, ninth or tenth specific embodiment above.

In a twelfth specific embodiment, Formula (III'), (III), (MA') or (IIIA), DM is represented by Formula (IIA) described above; and the remainder of the variables is as defined in the second embodiment, or each of its alternative embodiments, or the fourth, fifth, sixth, seventh, eighth, ninth, tenth or eleventh specific embodiment above.

In a thirteenth specific embodiment, in formula (III'), (III), (MA') or (IIIA), $R_{10}$, $R_{11}$, $R_{12}$ and $R_{13}$ are all H; q is 0 or an integer from 1 to 5; r is an integer from 1 to 5; and the remainder of the variables is as defined in the second embodiment, or each of its alternative embodiments, or the fourth, fifth, sixth, seventh, eighth, ninth, tenth, eleventh or twelfth specific embodiment above.

In a fourteenth specific embodiment, in Formula (III) or (IIIA), the conjugate is represented by any one of the following formulae, or a pharmaceutically acceptable salt thereof:

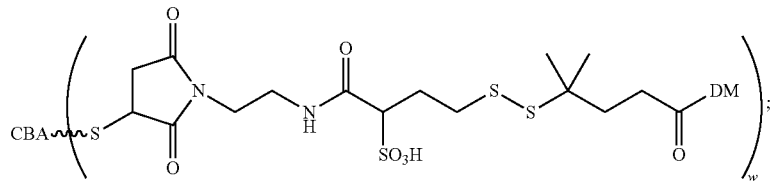

(IIIB)

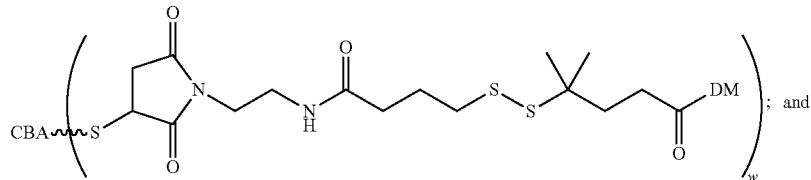

(IIIC)

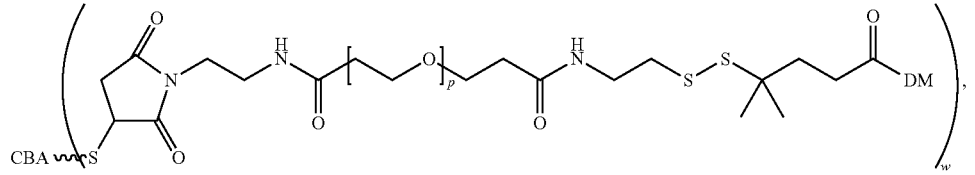

(IIID)

in which the CBA is as defined in the first embodiment above, and DM is a drug moiety represented by Formula (II) or (IIA) above. Preferably, p in Formula (IIID) is an integer from 1 to 24, or 2 to 8. More preferably, p is 2, 4, 8, 16 or 24.

In Formula (I), (IA), (III'), (III), (IIIA'), (IIIA), (IIIB), (IIIC), or (IIID), w is preferably an integer between 1 and 10, between 1 and 6, or alternatively, between 1 and 4; and the remainder of the variables is as defined in the first or second embodiment, or each of the embodiments above alternative to the first or second embodiment, or the first, second, third, fourth, fifth, sixth, seventh, eighth, ninth, ten, eleventh, twelfth, thirteenth or fourteenth specific embodiment above.

Cytotoxic Compounds

The present invention also provides a cytotoxic compound represented by Formula (IV') or (IV) as described in the third embodiment and its alternative embodiments above. In addition, eleven specific embodiments for the cytotoxic compound are further described below in this cytotoxic compound section.

In a first specific embodiment, in Formula (IV), the cytotoxic compound is represented by the following formula, or a salt (e.g., a pharmaceutically acceptable salt):

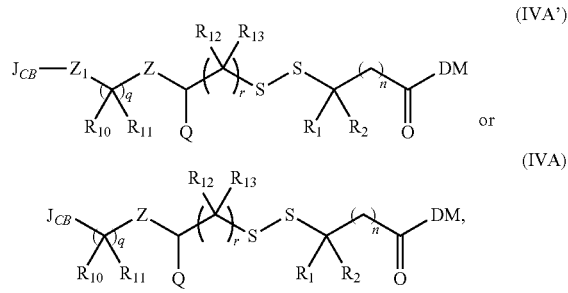

in which $R_1$ and $R_2$, for each occurrence, are independently H or an optionally substituted alkyl, n is an integer between 0 and 10, and the remainder of the variables is as defined in the third embodiment, or each of its alternative embodiments. Preferably, $R_1$ and $R_2$ are both methyl; and n is 2.

In a second specific embodiment, in Formula (IV'), (IV), (IVA') or (IVA), Q is i) H; ii) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a salt (e.g., a pharmaceutically acceptable salt) thereof; or, iii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene, or an optionally substituted phenylene; R$_{14}$ to R$_{16}$ are each independently an optionally substituted alkyl; and X$^-$ is an anion (e.g., a pharmaceutically acceptable anion). In this second specific embodiment, the remainder of the variables is as defined in the third embodiment, or each of its alternative embodiments, or its first specific embodiment.

In a third specific embodiment, variable Z' set forth in the preceding paragraph immediately above is alkylene, and the remainder of the variables is as defined in the third embodiment, or each of its alternative embodiments, or its first or second specific embodiment.

In a fourth specific embodiment, in Formula (IV'), (IV), (IVA') or (IVA), J$_{CB}$ is maleimide

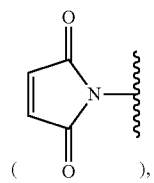

X'—CR$^b$R$^c$—C(=O)—, X'—CR$^b$R$^c$—C(=O)—NR$^e$—, R$^a$—C(=O)—, R$^a$—C(=O)-phenylene-, NH$_2$—NR$^e$—, NH$_2$—NR$^e$-phenylene-, NH$_2$—O—, —N$_3$, —C≡CH,

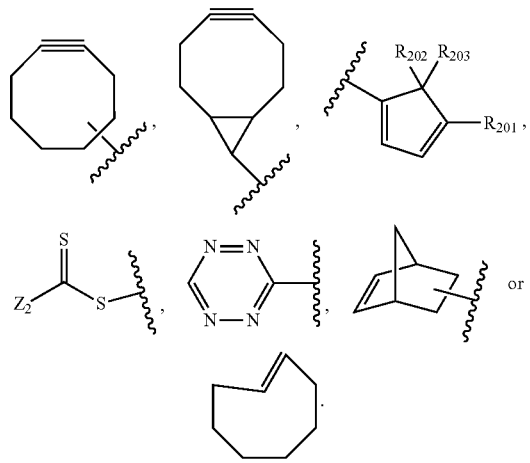

In this fourth specific embodiment, the remainder of the variables is as defined in the third embodiment, or each of its alternative embodiments, or its first, second, or third specific embodiment.

In a fifth specific embodiment, in Formula (IV'), (IV), (IVA') or (IVA), J$_{CB}$ is maleimide

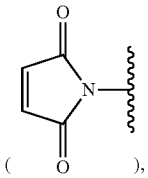

and the remainder of the variables is as defined in the third embodiment, or each of its alternative embodiments, or its first, second, or third specific embodiment.

In a sixth specific embodiment, in Formula (IV'), (IV), (IVA') or (IVA), Z is —C(=O)—NR$_9$— or —NR$_9$—C(=O)—, and the remainder of the variables is as defined in the third embodiment, or each of its alternative embodiments, or its first, second, third, fourth, or fifth specific embodiment.

In a seventh specific embodiment, in Formula (IV'), (IV), (IVA') or (IVA), R$^a$, R$^b$, R$^c$, and R$^e$ are each H; Z' is an optionally substituted alkylene (preferably unsubstituted alkylene); R$_9$ is H; and the remainder of the variables is as defined in the third embodiment, or each of its alternative embodiments, or its first, second, fourth, fifth, or sixth specific embodiment.

In an eighth specific embodiment, in Formula (IV'), (IV), (IVA') or (IVA), Q is H, or —SO$_3$H or a salt (e.g., a pharmaceutically acceptable salt) thereof; and the remainder of the variables is as defined in the third embodiment, or each of its alternative embodiments, or its first, second, fourth, fifth, sixth, or seventh specific embodiment.

In a ninth specific embodiment, in Formula (IV'), (IV), (IVA') or (IVA), DM is represented by Formula (IIA), and the remainder of the variables is as defined in the third embodiment, or each of its alternative embodiments, or its first, second, fourth, fifth, sixth, seventh or eighth specific embodiment.

In a tenth specific embodiment, in formula (IV'), (IV), (IVA') or (IVA), R$_{10}$, R$_{11}$, R$_{12}$ and R$_{13}$ are all H; q is 0 or an integer from 1 to 5; r is an integer from 1 to 5; and the remainder of the variables is as defined in the third embodiment, or each of its alternative embodiments, or the fourth, fifth, sixth, seventh, eighth or ninth specific embodiment above.

In a eleventh specific embodiment, in Formula (IV) or (IVA), the cytotoxic compound is represented by any one of the following formulae, or a salt (e.g., a pharmaceutically acceptable salt) thereof:

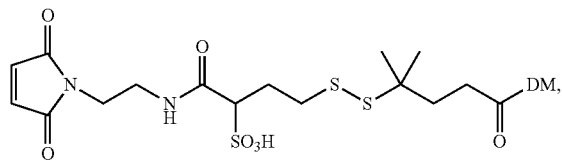 (IVB)

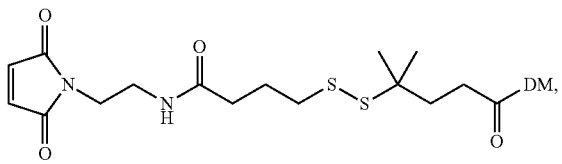 (IVC)

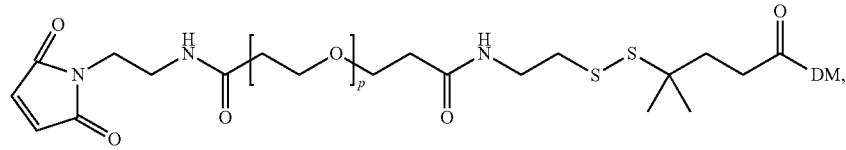 (IVD)

in which DM is a drug moiety represented by Formula (II) or (IIA) above. Preferably, p in Formula (IVD) is an integer from 1 to 24, or 2 to 8. More preferably, p is 2, 4, 8, 16 or 24.

Linker Compounds

The present invention further provides a linker compound represented by Formula (V) as described in the fourth embodiment and its alternative embodiments above. In addition, eleven specific embodiments for the linker compound are further described below in this linker compound section.

In a first specific embodiment, in Formula (V') or (V), $J_D$ is —SH or —SSR$^d$, and the remainder of the variables is as defined in the fourth embodiment, or each of its alternative embodiments.

In a second specific embodiment, in Formula (V') or (V), Q is i) H; ii) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a salt (e.g., a pharmaceutically acceptable salt) thereof; or, iii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; R$_{14}$ to R$_{16}$ are each independently an optionally substituted alkyl; and X$^-$ is an anion (e.g., a pharmaceutically acceptable anion). In this second specific embodiment, the remainder of the variables is as defined in the fourth embodiment, or each of its alternative embodiments, or its first specific embodiment.

In a third specific embodiment, variable Z' set forth in the preceding paragraph immediately above is alkylene, and the remainder of the variables is as defined in the fourth embodiment, or each of its alternative embodiments, or its first or second specific embodiment.

In a fourth specific embodiment, in Formula (V') or (V), $J_{CB}$ is maleimide

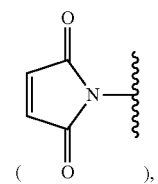

X'—CR$^b$R$^c$—C(=O)—, X'—CR$^b$R$^c$—C(=O)—NR$^e$—, R$^a$—C(=O)—, R$^a$—C(=O)-phenylene-, NH$_2$—NR$^e$—, NH$_2$—NR$^e$-phenylene-, NH$_2$—O—, —N$_3$, —C≡CH,

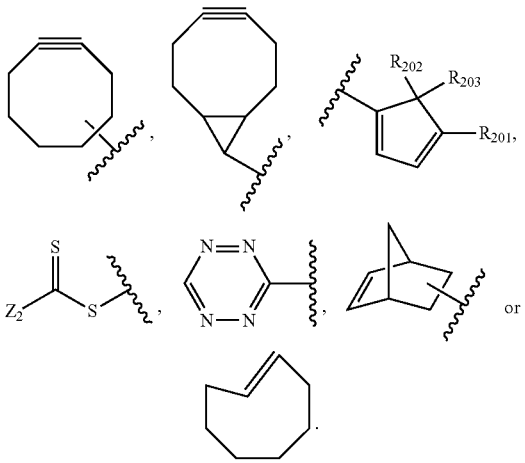

In this fourth specific embodiment, the remainder of the variables is as defined in the fourth embodiment, or each of its alternative embodiments, or its first, second, or third specific embodiment.

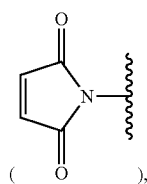

In a fifth specific embodiment, in Formula (V') or (V), $J_{CB}$ is maleimide and the remainder of the variables is as defined in the fourth embodiment, or each of its alternative embodiments, or its first, second, or third specific embodiment.

In a sixth specific embodiment, in Formula (V') or (V), Z is —C(=O)—NR$_9$— or —NR$_9$—C(=O)—, and the remainder of the variables is as defined in the fourth embodiment, or each of its alternative embodiments, or its first, second, third, fourth, or fifth specific embodiment.

In a seventh specific embodiment, in Formula (V') or (V), R$^a$, R$^b$, R$^c$, and R$^e$ are each H; Z' is an optionally substituted alkylene (preferably unsubstituted alkylene); R$_9$ is H; and the remainder of the variables is as defined in the fourth embodiment, or each of its alternative embodiments, or its first, second, fourth, fifth, or sixth specific embodiment.

In an eighth specific embodiment, in Formula (V') or (V), Q is H, or —SO$_3$H, or a salt (e.g., a pharmaceutically acceptable salt) thereof; and the remainder of the variables is as defined in the fourth embodiment, or each of its alternative embodiments, or its first, second, fourth, fifth, sixth, or seventh specific embodiment.

In a ninth specific embodiment, in formula (V') or (V), R$_{10}$, R$_{11}$, R$_{12}$ and R$_{13}$ are all H; q is 0 or an integer from 1 to 5; r is an integer from 1 to 5; and the remainder of the variables is as defined in the fourth embodiment, or each of its alternative embodiments, or the fourth, fifth, sixth, seventh or eighth specific embodiment above.

In a tenth specific embodiment, in Formula (V), the linker compound is represented by any one of the following formulae, or a salt (e.g., a pharmaceutically acceptable salt) thereof:

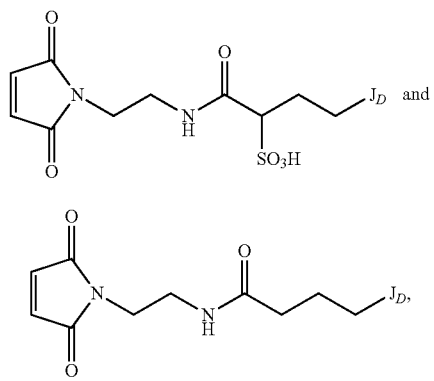

(VA) and (VB)

in which J$_D$ is —SSR$^d$ or —SC(=O)R$^g$; and, alternatively J$_D$ is —SSR$^d$. Preferably, J$_D$ is —SSPy (Py is pyridyl).

In a eleventh specific embodiment, the present invention provides a compound represented by the following formula:

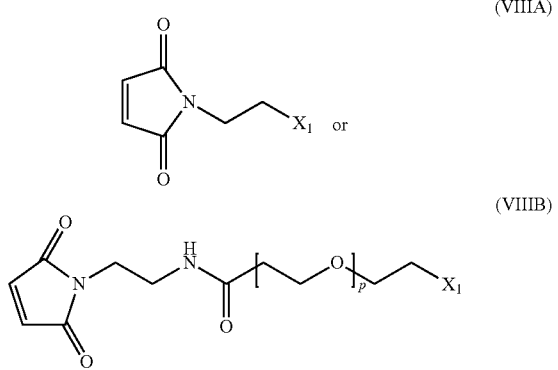

(VIIIA) or (VIIIB)

wherein X$_1$ is —COOH or an reactive ester. The compound of Formula (VIIIA) or (VIIIB) can be used to prepare a linker compound or a cytotoxic compound of the present invention, e.g., as shown below:

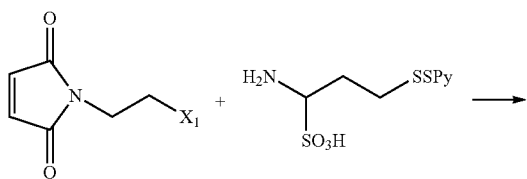

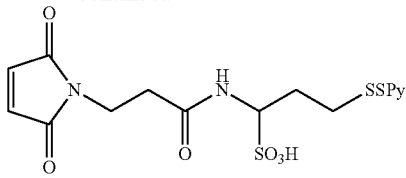

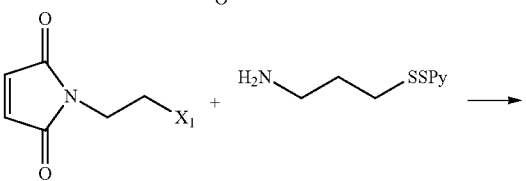

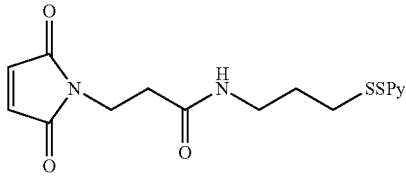

Preferably, X$_1$ is —COOH or N-hydroxysuccinimide ester

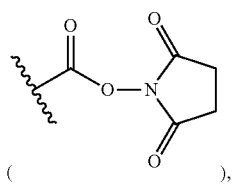 [SMILES: *C(=O)ON1C(=O)CCC1=O]

( ),

Modified Cell-Binding Agent

The present invention further provides a modified cell-binding agent represented by Formula (VI') or (VI) as described in the fifth embodiment and its alternative embodiments above. In addition, ten specific embodiments for the linker compound are further described below in this linker compound section.

In a first specific embodiment, in Formula (VI') or (VI), J$_D$ is —SH or —SSR$^d$, and the remainder of the variables is as defined in the fifth embodiment, or each of its alternative embodiments. Preferably, J$_D$ is —SSPy, wherein Py is a pyridyl.

In a second specific embodiment, in Formula (VI') or (VI), Q is i) H; ii) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a salt (e.g., a pharmaceutically acceptable salt) thereof; or, iii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; R$_{14}$ to R$_{16}$ are each independently an optionally substituted alkyl; and X$^-$ is an anion (e.g., a pharmaceutically acceptable anion). In this second specific embodiment, the remainder of the variables is as defined in the fifth embodiment, or each of its alternative embodiments, or its first specific embodiment.

In a third specific embodiment, variable Z' set forth in the preceding paragraph immediately above is alkylene, and the remainder of the variables is as defined in the fifth embodiment, or each of its alternative embodiments, or its first or second specific embodiment.

In a fourth specific embodiment, in Formula (VI') or (VI), J$_{CB'}$ is

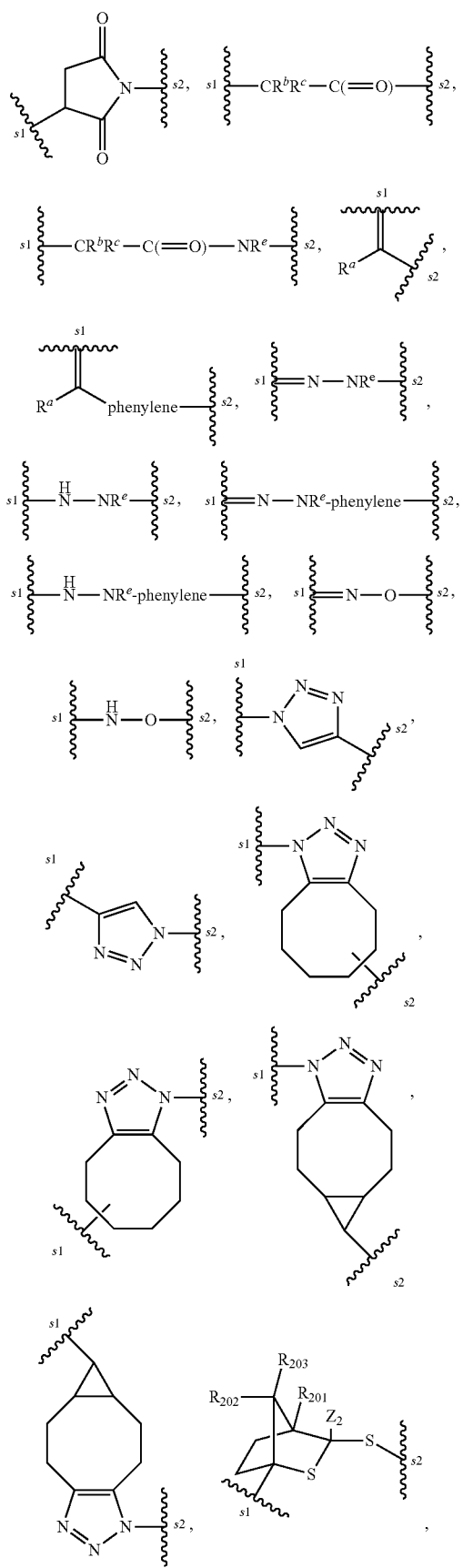

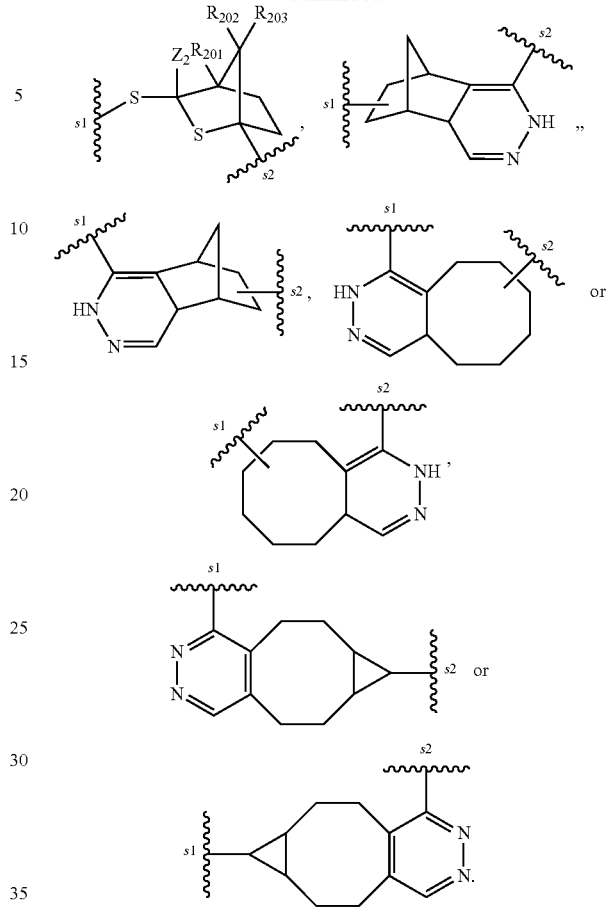

In this fourth specific embodiment, the remainder of the variables is as defined in the fifth embodiment, or each of its alternative embodiments, or the first, second or third specific embodiment above.

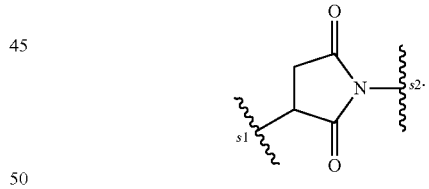

In an fifth specific embodiment, in Formula (VI') or (VI), $J_{CB'}$ is and the remainder of the variables is as defined in the fifth embodiment, or each of its alternative embodiments, or the first, second or third specific embodiment above.

In a sixth specific embodiment, in Formula (VI') or (VI), Z is —C(=O)—NR$_9$— or —NR$_9$—C(=O)—, and the remainder of the variables is as defined in the fifth embodiment, or each of its alternative embodiments, or the first, second, third, fourth or fifth specific embodiment.

In a seventh specific embodiment, in Formula (VI') or (VI), $R^a$, $R^b$, $R^c$, and $R^e$ are each H; Z' is an optionally substituted alkylene (preferably unsubstituted alkylene); R$_9$ is H; and the remainder of the variables is as defined in the fifth embodiment, or each of its alternative embodiments, or the first, second, third, fourth, fifth or sixth specific embodiment above.

In an eighth specific embodiment, in Formula (VI') or (VI), Q is H, or —SO₃H or a pharmaceutically acceptable salt thereof; and the remainder of the variables is as defined in the fifth embodiment, or each of its alternative embodiments, or the first, second, third, fourth, fifth, sixth or seventh specific embodiment above.

In a ninth specific embodiment, in formula (VI') or (VI), $R_{10}$, $R_{11}$, $R_{12}$ and $R_{13}$ are all H; q is 0 or an integer from 1 to 5; r is an integer from 1 to 5; and the remainder of the variables is as defined in the fifth embodiment, or each of its alternative embodiments, or the fourth, fifth, sixth, seventh or eighth specific embodiment above.

In a tenth specific embodiment, in Formula (VI') or (VI), the modified cell-binding agent is represented by any one of the following formulae, or a pharmaceutically acceptable salt thereof:

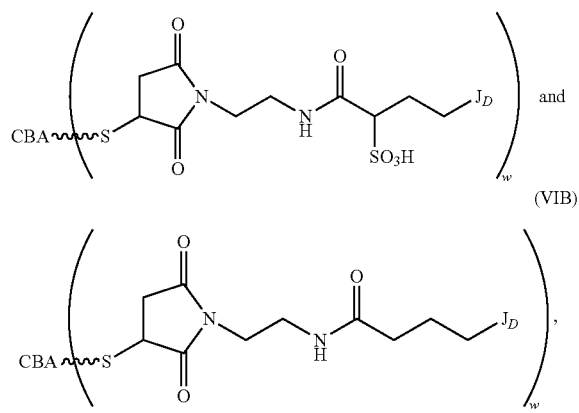

in which the CBA is as defined in the first embodiment above, and $J_D$ is —SH, —SSR$^d$ or —SC(=O)R$^g$; and, alternatively $J_D$ is —SH or —SSR$^d$. Preferably, $J_D$ is —SH or —SSPy (Py is pyridyl).

In Formula (VI'), (VI), (VIA) or (VIB), w is preferably an integer between 1 and 10, between 1 and 6, or alternatively, between 1 and 4; and the remainder of the variables is as defined in the fifth embodiment, or each of the embodiments above alternative to the fifth embodiment, or the first, second, third, fourth, fifth, sixth, seventh, eighth, ninth or tenth specific embodiment above.

Production of Cell-Binding Agent-Drug Conjugates

The conjugates of the present invention can be prepared according to any known method in the art. See, for example, WO 2009/134977, U.S. Pat. Nos. 7,811,572, 6,441,163, 7,368,565, 8,163,888, U.S Publication Nos. 2006/0182750, 2011/0003969, 2012/0253021 and Widdison, W. C. et al. "Semisynthetic maytansine analogues for the targeted treatment of cancer," J. Med. Chem. (2006) 49(14):4392-4408. In one embodiment, the conjugates of the present invention can be prepared by reacting a cell-binding agent with a drug-linker compound (e.g., compounds of Formula (IV') or (IV)) having a reactive moiety capable of forming a covalent bond with the cell-binding agent to form a cell-binding agent-cytotoxic agent conjugate. The conjugate can then be purified. The drug-linker compound can be generated in situ and used to react with the antibody without purification. Alternatively, the drug-linker compound can be generated and purified before conjugating to the cell-binding agent. In another embodiment, the conjugates of the present invention can be prepared by: a) reacting a cell-binding agent with a linker compound (e.g., compounds of Formula (V') or (V)) to form a modified cell-binding agent having the linkers covalently bound thereto (e.g., Formula (VI') or (VI); b) optionally purifying the modified cell-binding agent; c) conjugating a cytotoxic agent (e.g., Formula (VII), (VIIA), (VIIB) or (VIIC)) to the modified cell-binding agent to form the cell-binding agent-cytotoxic compound conjugate of the present invention; and d) purifying the cell-binding agent-cytotoxic compound conjugate. In one embodiment, the cytotoxic agent is represented by the following formula, or a salt thereof:

In Formula (VII), Y and DM are as defined in the first embodiment; and $J_D$ is as defined in the fourth embodiment. Preferably, the cytotoxic agent of Formula (VII) is represented by the following formula, or a salt thereof:

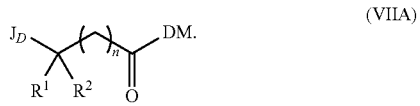

More preferably, the cytotoxic agent is represented by the following formula, or a salt thereof:

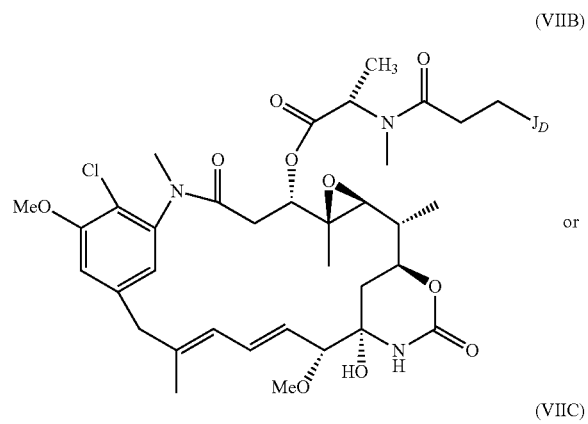

or

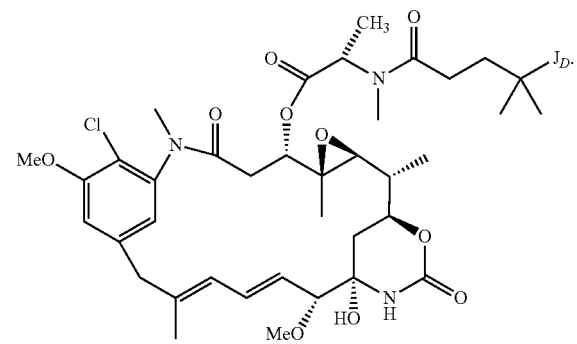

Preferably, in Formula (VII), (VIIA), (VIIB) or (VIIC), $J_D$ is —SH or —SSR$^d$. Even more preferably, $J_D$ is —SH or —SSPy.

In another embodiment, the conjugate of the present invention can be prepared by mixing together a cell-binding agent, a cytotoxic agent and a linker compound. Preferably, the cell-binding agent is contacted with a cytotoxic agent first to form a mixture comprising the cell-binding agent and the cytotoxic agent, followed by contacting the mixture with a linker compound (e.g., compounds of Formula (V') or (V)) to form the cell-binding agent-cytotoxic compound conjugate. The conjugate can then be purified. In one embodiment, the cytotoxic agent is represented by formula (VII), (VIIA), (VIIB) or (VIIC), wherein the definitions of variables and their preferred values are as described above.

Any purification methods known in the art can be used to purify the conjugates of the present invention (See, for example, *Bioconjugate Techniques*, 2nd Edition by Greg T. Hermanson, published by Academic Press, Inc., 2008). In one embodiment, the conjugates of the present invention can be purified using tangential flow filtration (TFF), non-adsorptive chromatography, adsorptive chromatography, adsorptive filtration, selective precipitation, high performance liquid chromatography (HPLC), dialysis or any other suitable purification process, as well as combinations thereof.

Any suitable TFF systems may be utilized for purification, including a Pellicon type system (Millipore, Billerica, Mass.), a Sartocon Cassette system (Sartorius A G, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., Mab-Select, GE Healthcare, Piscataway, N.J.), His-Tag metal affinity resins, anti-FLAG affinity resins, and lectin affinity resins, e.g. Lentil Lectin Sepharose resin (GE Healthcare, Piscataway, N.J.), where the antibody bears appropriate lectin binding sites. Examples of suitable reversed phase resins include C4, C8, and C18 resins (Grace Vydac, Hesperia, Calif.).

Any suitable non-adsorptive chromatography resin may be utilized for purification. For example, size-exclusion chromatography can be used for purifying the conjugates of the invention. Examples of suitable non-adsorptive chromatography resins include, but are not limited to, SEPHADEX™ G-10, G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In one embodiment, when the cell-binding agent is an epitope-tagged Avibody, the conjugate can be purified using hydroxyl apatite chromatography, size-exclusion chromatography, tangential flow filtration, gel electrophoresis, dialysis, and affinity chromatography, preferably affinity chromatography, more preferably His-tag metal affinity chromatography and anti-FLAG M2 affinity chromatography (see, for example, US 2008/0152586 and US 2012/0171115).

In another embodiment, when the cell-binding agent is a centyrin, the conjugate can be purified using protein A purification, ammonium sulfate or ethanol precipitation, acid extraction, anion or cation exchange chromatography, phosphocellulose chromatography, hydrophobic interaction chromatography, size-exclusion chromatography, tangential flow filtration, affinity chromatography, hydroxylapatite chromatography and lectin chromatography. Alternatively, the conjugate can be purified using HPLC. Preferably, the conjugate can be purified by using affinity chromatography, more preferably His-tag metal affinity chromatography. See, for example, US Patent Publication Nos. US 2010/0255056, US 2010/0216708 and US 2011/0274623.

In another embodiment, when the cell-binding agent is a DARPin, the conjugate can be purified by affinity chromatography, size exclusion chromatography, hydroxylapatite chromatography, tangential flow filtration, preferably affinity chromatography, more preferably His-Tag affinity chromatography. See, for example, U.S. Patent Publication Nos. 20040132028, 2009/0082274, 2011/0118146, and 2011/0224100, WO 02/20565 and WO 06/083275.

The number of cytotoxic compound molecule bound per cell-binding agent (e.g., antibody) molecule can be determined spectroscopically by measuring the ratio of the absorbance at 280 nm and 252 nm. An average of about 0.5- about 20 cytotoxic compounds/antibody molecule(s) can be linked by the methods described herein. In one embodiment, the average number of linked cytotoxic compound per cell-binding agent in the conjugate (i.e., average w value) is about 0.5 to about 10, about 0.5 to 2 (e.g., 0.4, 0.5, 0.6, 0.7, 0.8, 0.9, 1.0, 1.1, 1.2, 1.3, 1.4, 1.5, 1.6, 1.7, 1.8, 1.9, 2.0, or 2.1), about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 5.0 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0), about 2.5 to about 4.0, about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In Vitro Evaluation of Cytotoxicity

The cytotoxic compounds and cell-binding agent-drug conjugates of the invention can be evaluated for their ability to suppress proliferation of various cancer cell lines in vitro. The in vitro cytotoxicity assays can be conducted using methods known in the art (e.g., Widdison, W. C. et al., "Semisynthetic maytansine analogues for the targeted treatment of cancer," *J. Med. Chem.* (2006) 49(14):4392-408). For example, cells to be evaluated can be exposed to the compounds or conjugates for 1-5 days and the surviving fractions of cells measured in direct assays by known methods. $IC_{50}$ values can then be calculated from the results of the assays.

Compositions and Methods of Use

The present invention includes a composition (e.g., a pharmaceutical composition) comprising conjugates (e.g., conjugates of Formula (I) or Formula (III') or (III)) or cytotoxic compounds (e.g., compounds of Formula (IV') or (IV)) described herein, and a carrier (a pharmaceutically acceptable carrier). The present invention also includes a composition (e.g., a pharmaceutical composition) comprising the conjugate of Formula (I), (III') or (III), or the cytotoxic compound of Formula (IV') or (IV), and a carrier (a pharmaceutically acceptable carrier), and further comprising a second therapeutic (e.g., chemotherapeutic) agent. The present compositions are useful for inhibiting abnormal cell growth or treating a proliferative disorder in a mammal (e.g., human). The present compositions are also useful for treating an autoimmune disorder, a destructive bone disorder, a graft versus host disease, a transplant rejection, an immune deficiency, an inflammatory disease, an infectious disease, a viral disease, a fibrotic disease, a neurodegenerative disorder, a pancreatitis or kidney disease in a mammal (e.g., human).

The present invention includes a method of inhibiting abnormal cell growth or treating a proliferative disorder in a mammal (e.g., human) comprising administering to said mammal a therapeutically effective amount of conjugates (e.g., conjugates of Formula (I), (III') or (III)) or cytotoxic compounds (e.g., compounds of Formula (IV') or (IV)) described herein, or a composition thereof, alone or in combination with a second therapeutic (e.g., chemotherapeutic) agent. In one embodiment, the proliferative disorder is cancer in general; alternatively, the proliferative disorder is cancer selected from the group consisting of breast cancer, colon cancer, brain cancer, prostate cancer, kidney cancer, pancreatic cancer, ovarian cancer, head and neck cancer, melanoma, colorectal cancer, gastric cancer, squamous cancer, small-cell lung cancer, nonsmall-cell lung cancer, testicular cancer, Merkel cell carcinoma, glioblastoma, neuroblastoma, a cancer of a lymphatic organ, and a hematological malignancy.

Similarly, the present invention provides a method for inducing cell death in selected cell populations comprising contacting target cells or tissue containing target cells with an effective amount of the conjugates of the present invention. The target cells are cells to which the cell-binding agent of the conjugates can bind.

If desired, other active agents, such as other anti-tumor agents, may be administered along with the conjugate.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include: Comprehensive index; Manufacturer; Products (by company's or trademarked drug name); Category index; Generic/chemical index (non-trademark common drug names); Color images of medications; Product information, consistent with FDA labeling; Chemical information; Function/action; Indications & Contraindications; Trial research, side effects, warnings.

The present invention also provides methods of treating a non-cancerous condition comprising administering to a subject in need of treatment an effective amount of any of the conjugates described above. Examples of the conditions include, but not limited to, an autoimmune disorder (e.g., systemic lupus, rheumatoid arthritis, and multiple sclerosis), a graft versus host disease, a transplant rejection (e.g., a renal transplant rejection, a liver transplant rejection, a lung transplant rejection, a cardiac transplant rejection, and a bone marrow transplant rejection), an immune deficiency, an inflammatory diseases (i.e., myositis and pancreatitis), a destructive bone disorder, an infectious disease (e.g., viral infections and parasite infections), a viral disease, a fibrotic disease, a neurodegenerative disorder, or a kidney disease. In one embodiment, the condition selected from the group consisting of cancer, rheumatoid arthritis, multiple sclerosis, graft versus host disease, transplant rejection, lupus, myositis, infectious disease, and immune deficiency.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic compounds or conjugates of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 ml of normal saline to which 5 to 10 ml of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Suitable pharmaceutically acceptable carriers, diluents, and excipients are well known and can be determined by those of ordinary skill in the art as the clinical situation warrants. Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

Example 1

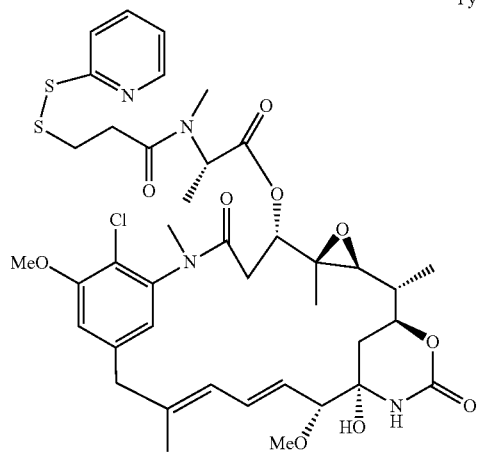

PyS-DM1

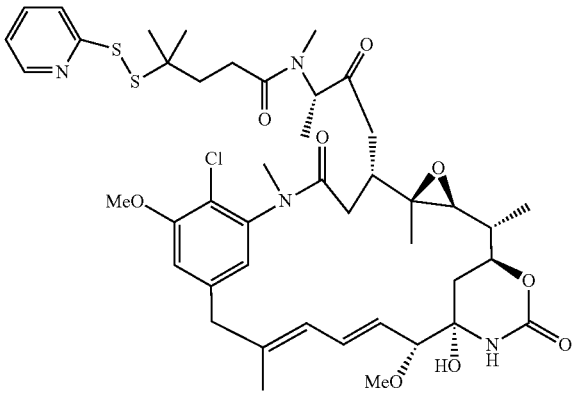

PyS-DM4

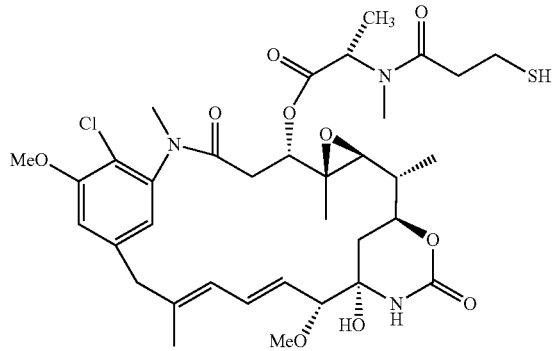

DM1

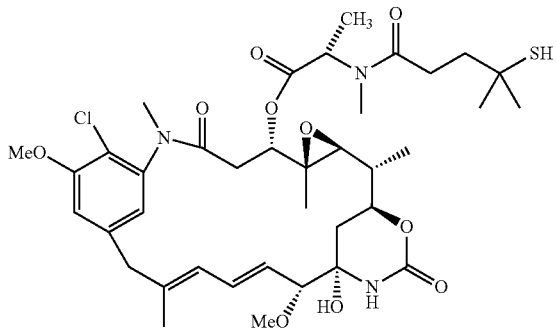

DM4

Maytansinoids containing a reactive disulfide can be prepared by reacting 2,2'-dithiopyridine with a thiol-bearing maytansinoid such as DM1 or DM4. DM1 and DM4 can be prepared, for example, according to procedures described in U.S. Pat. Nos. 7,301,019 and 7,598,375. Reaction of DM1 with 2,2'-dithiopyridine will give PyS-DM1 and reaction of 2,2'-dithiopyridine with DM4 will give PyS-DM4.

Synthesis of PyS-DM1

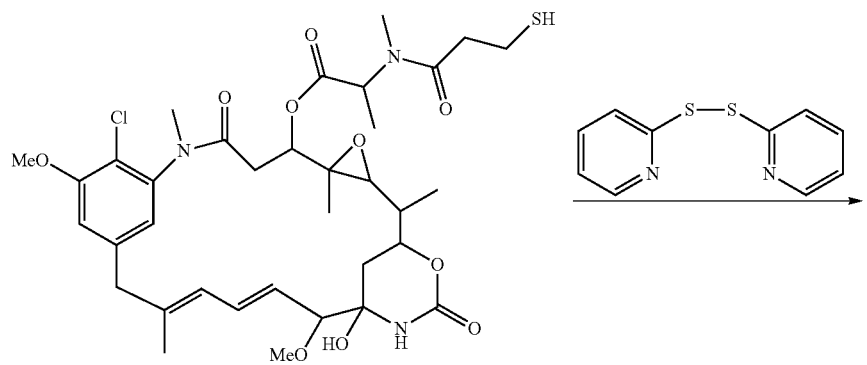

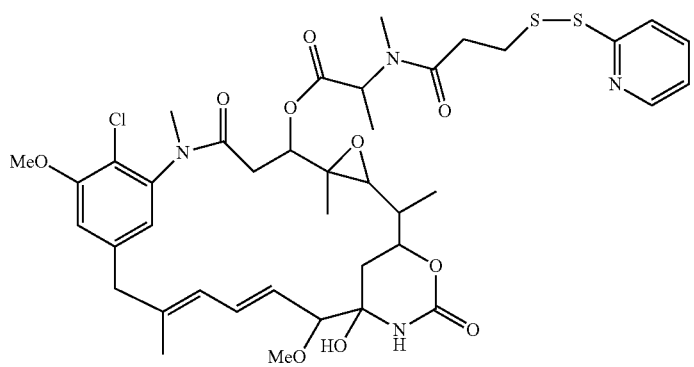

DM1 (100 mg, 0.14 mmol) was dissolved in dimethoxyethane (4 mL) and added to a magnetically stirred solution of 2,2'-dithiodipyridine (100 mg, 0.45 mmol) in dimethoxyethane (4 mL) containing acetic acid (0.4 mL). After 2 hours the reaction was purified by silica chromatography on a 20 g cartridge eluting with dichloromethane and a linear gradient from 3% to 8% methanol over 25 min. Desired product was collected and solvent evaporated under vacuum to give 104 mg (87 yield) of desired product. MS (M+H)$^+$ found 847.6; calcd. 847.3.

Synthesis of PyS-DM4

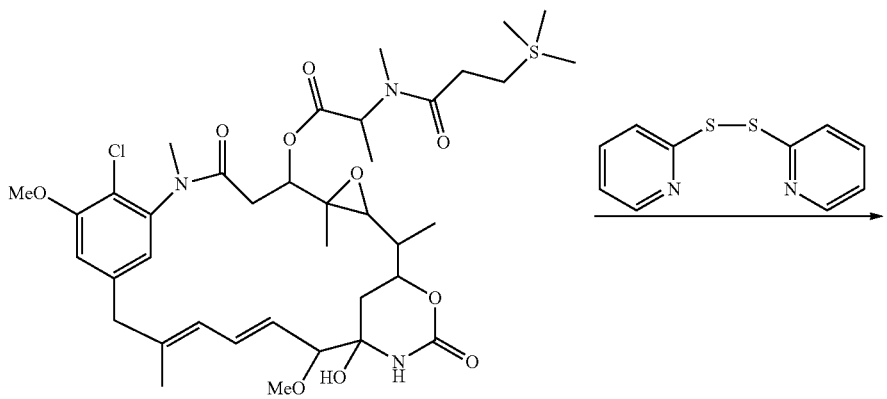

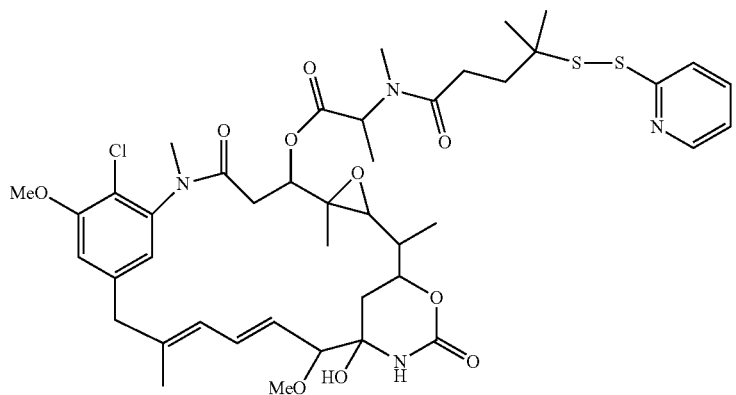

DM4 (94 mg, 0.12 mmol) was dissolved in dimethoxyethane (4 mL) and added to a magnetically stirred solution of 2,2'-dithiodipyridine (100 mg, 0.45 mmol) in dimethoxyethane (4 mL) containing acetic acid (0.4 mL). After 2 hours the reaction was purified by silica chromatography on a 20 g cartridge eluting with dichloromethane and a linear gradient from 3% to 8% methanol over 25 min. Desired product was collected and solvent evaporated under vacuum to give 90 mg (84% yield) of desired product. MS (M+H)$^+$ found 889.7; calcd. 889.3.

Example 2

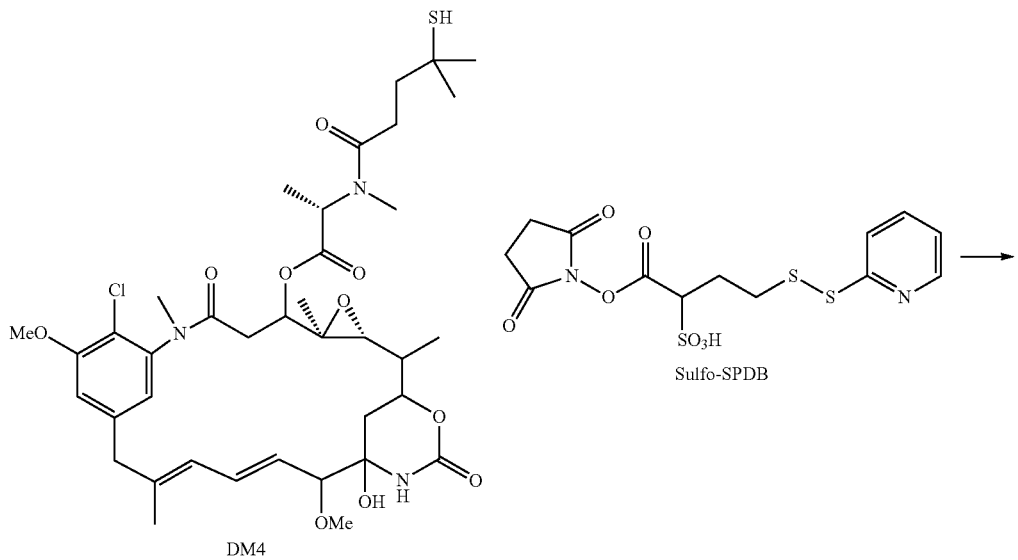

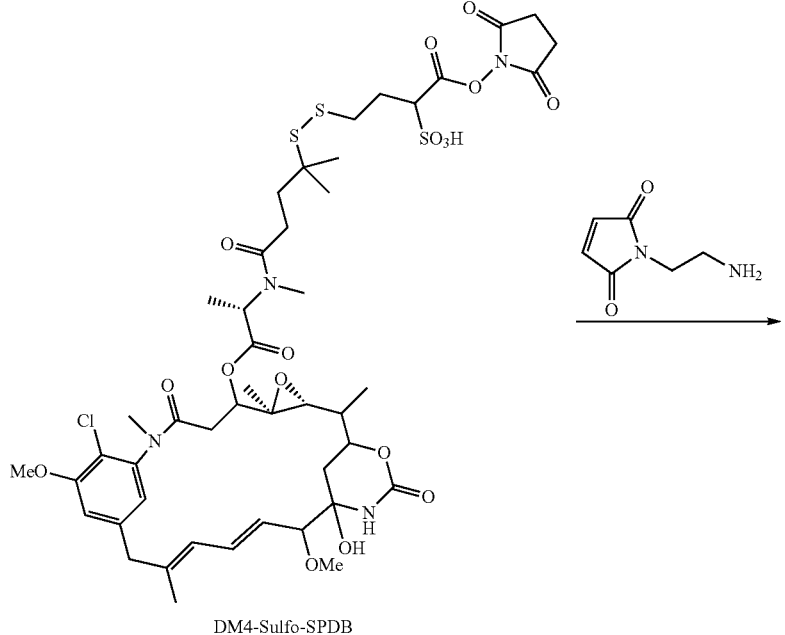

DM4-Sulfo-SPDB

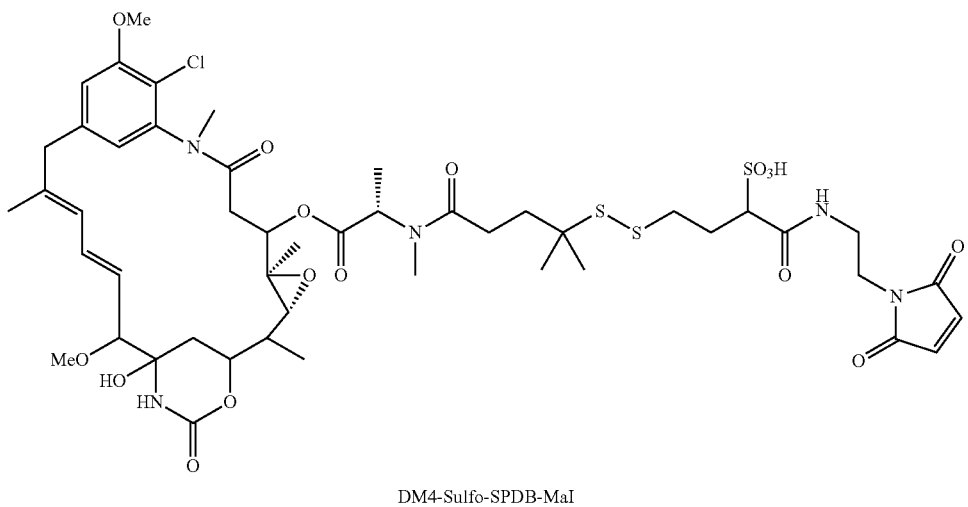

DM4-Sulfo-SPDB-Mal

Synthesis of DM4-Sulfo-SPDB-Mal

A solution of 14.6 mM DM4 in DMA (2 mL, 29.2 mmol) was treated with 1:1 solution of saturated sodium bicarbonate to water (5%, 219 µl) followed by Sulfo-SPDB (29.7 mg, 0.073 mmol) under argon at room temperature with HPLC/MS monitoring. After 1 hour DM4 was consumed to give DM4-Sulfo-SPDB-DM4. Low Resolution MS calcd. (M−1)=1073.2. found (M−1)=1073.2.

The reaction was treated with 1-(2-aminoethyl)-maleimide HCl (12.90 mg, 0.073 mmol) under argon. After 3 hour desired product was formed. The material was purified on semi-prep HPLC C8 column using Water with 0.2% formic acid and 0.1% TEA and Acetonitrile. Low resolution MS, calcd. (M−1)=1098.34. found (M−1)=1098.2.

Example 3
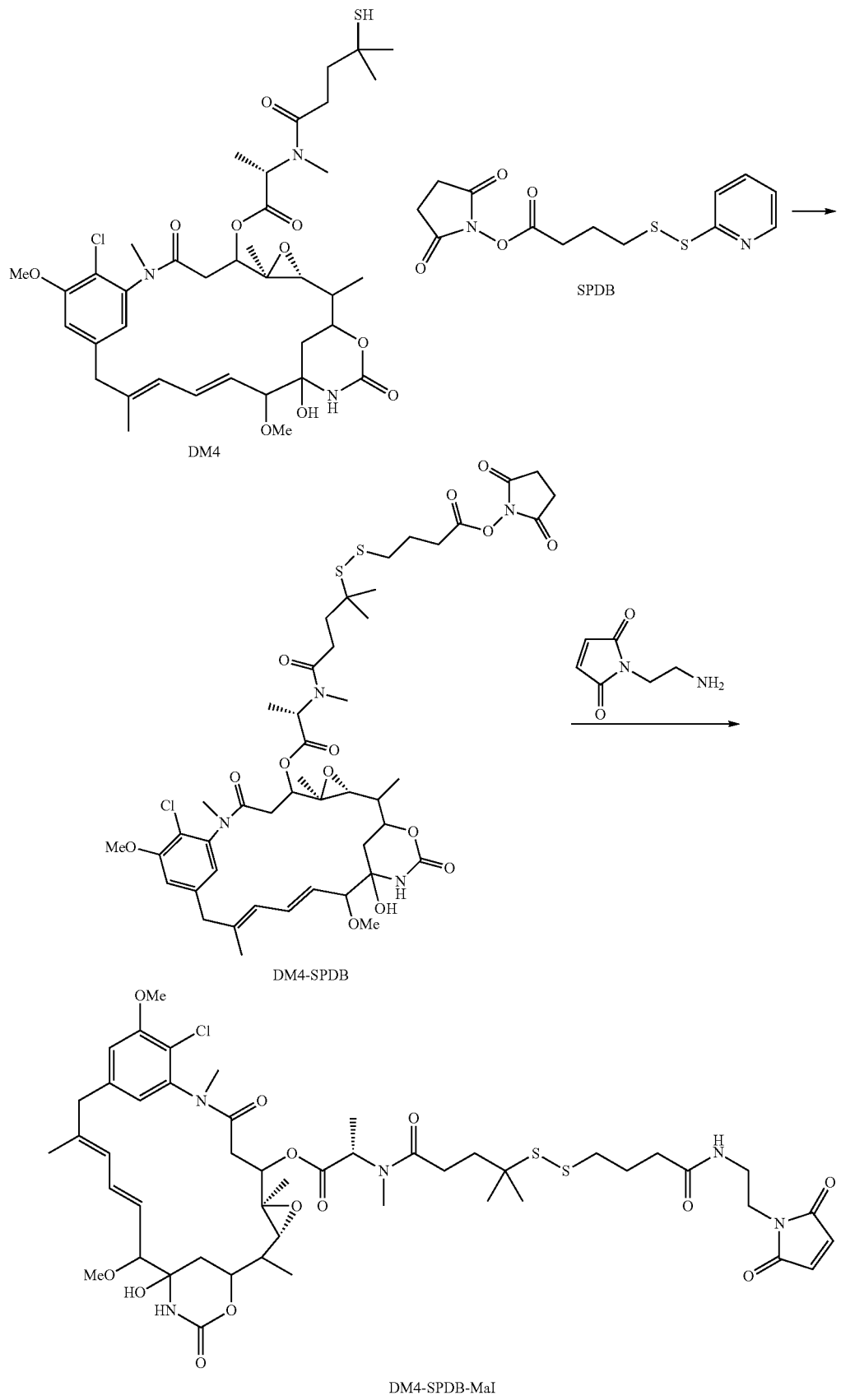

DM4-SPDB-Mal will be prepared according similar procedures described in Example 2 for DM4-sulfo-SPDB-Mal.

Example 4

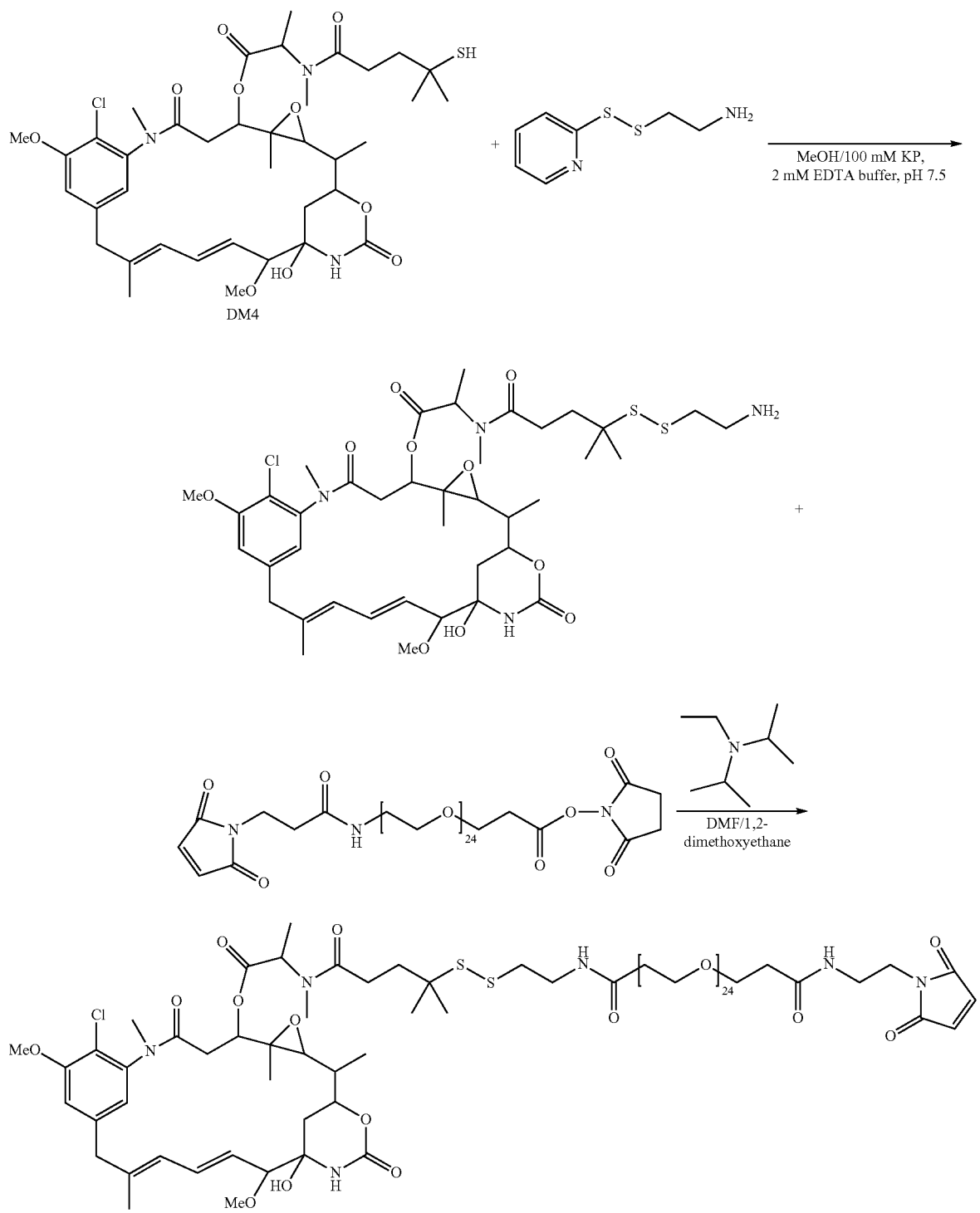

A 10 mL round bottom flask was charged with DM4 (52.5 mg, 0.067 mmol) and methanol (1.5 mL) to give a clear colorless solution. A solution of 2-(pyridin-2-yldisulfanyl) ethanamine (prepared in-house using established procedure, 13.79 mg, 0.074 mmol) in pH 7.5 100 mM KP, 2 mM EDTA buffer (1.5 mL) was then added. The reaction was stirred for 1 hour at room temperature and was then concentrated to a crude oil in vacuo. The desired product was isolated with 98.7% purity by semi-preparative RP-HPLC to give 32.8 mg (56.2% yield) of DM4-S(CH$_2$)$_2$—NH$_2$ as the formic acid salt. MS: m/z found: 877.1 (M+Na)$^+$ calculated: 877.3. found: 890.9 (M+Cl)$^-$, calculated: 889.3

Example 5
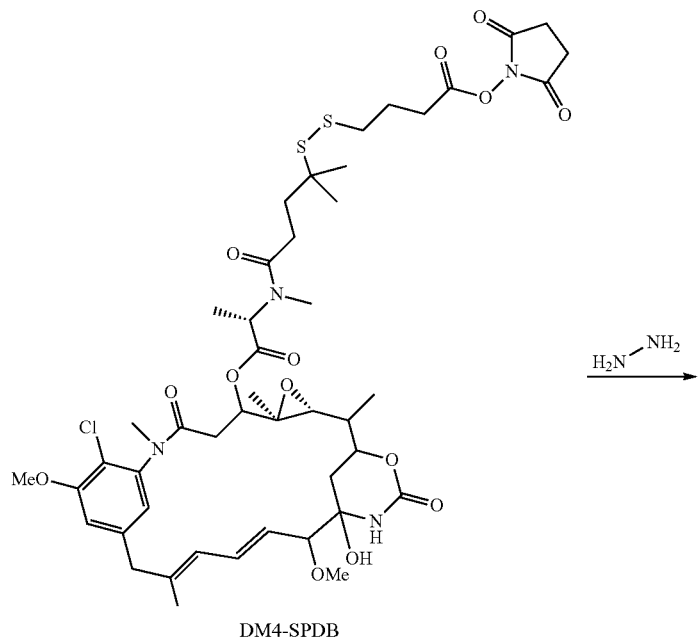
DM4-SPDB
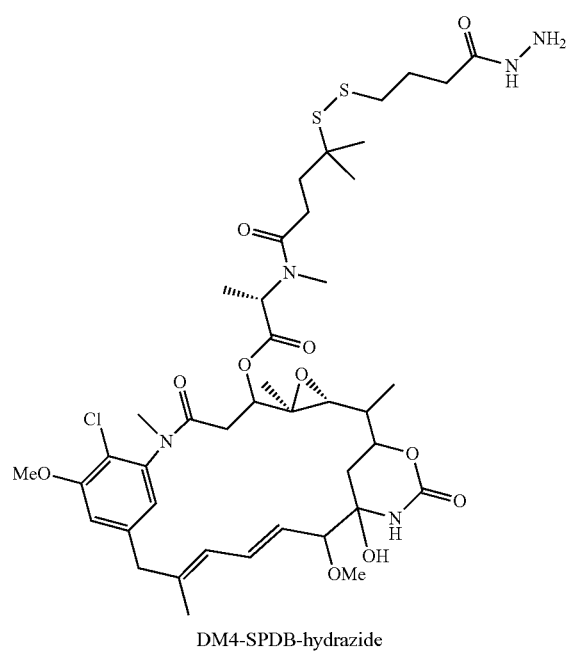
DM4-SPDB-hydrazide

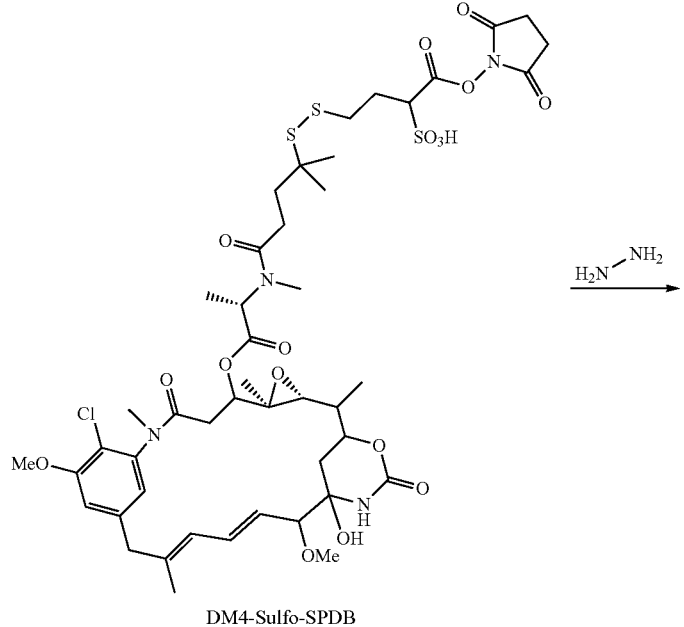

DM4-Sulfo-SPDB

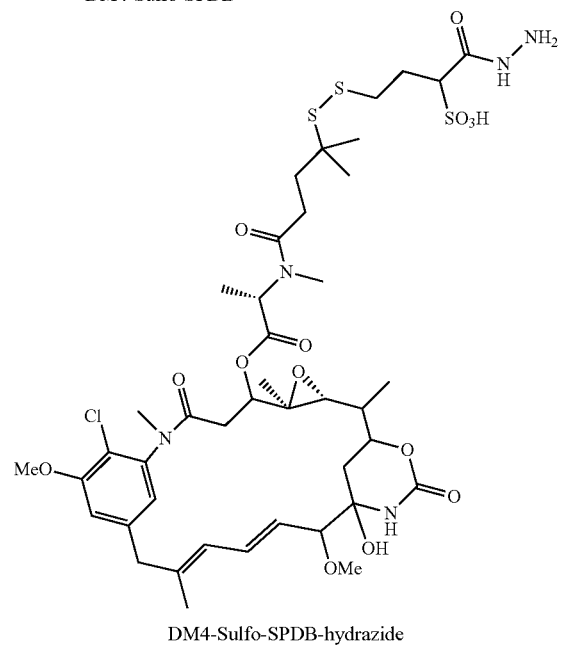

DM4-Sulfo-SPDB-hydrazide

DM4-SPDB-hydrazide and DM4-Sulfo-SPDB-hydrazide will be prepared by reacting DM4-SPDB or DM4-Sulfo-SPDB with hydrazine as shown above.

Example 6

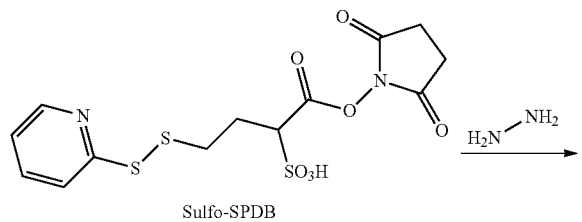

Sulfo-SPDB

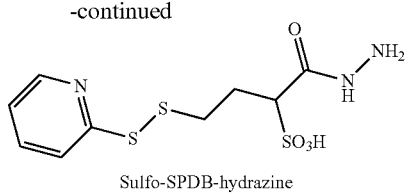

Sulfo-SPDB-hydrazine

Previously described sulfo-SPDB (U.S. Pat. No. 8,236,319) can be reacted with hydrazine to yield sulfo-SPDB-hydrozine linker.

To a 0.24M solution of hydrazine (0.015 ml, 0.242 mmol) in DMA was added a 0.06M solution of 1-((2,5-dioxopyr rolidin-1-yl)oxy)-1-oxo-4-(pyridin-2-yldisulfanyl)butane-2-sulfonic acid (25.9 mg, 0.0635 mmol) in DMA, dropwise with rapid stirring at room temperature. After stirring for 40 min under argon at 50° C., the crude reaction mixture was purified by reverse-phase HPLC (C18, 21.2×250 mm) eluting with deionized water containing 0.1% formic acid using an acetonitrile gradient 5-25% over 30 min. Fractions containing desired product were combined, frozen and lyophilized give 3.1 mg (15% yield) of desired product as a white solid. MS (M+1)$^+$ found: 324.05, calculated: 324.01. $^1$H NMR (400 MHz, DMSO-d6) δ 2.13-2.26 (m, 2H), 2.82-2.91 (m, 2H), 3.52 (t, J=7.8, 6.1 Hz, 1H), 7.24 (t, J=7.3, 4.7 Hz, 1H), 7.76 (d, J=8.0 Hz, 1H), 7.83 (t, 1H), 8.45 (d, J=3.5, 2.0 Hz, 1H).

The resulting compound can be reacted with an aldehyde or ketone-bearing cell binding agent then the hydrazide linkage can be optionally reduced. The resulting linker can be reacted with an aldehyde or ketone-bearing cell binding agent then reacted with a thiol bearing maytansinoid such as DM1 or DM4 to give conjugate.

Alternatively once the linker is reacted with the cell binding agent the reactive disulfide of the resulting molecule can be reduced using reagents such as dithiothreitol or TCEP to give a thiol which can be reacted with a maytansinoid-bearing a reactive disulfide such as PyS-DM1 or PyS-DM4.

Example 7

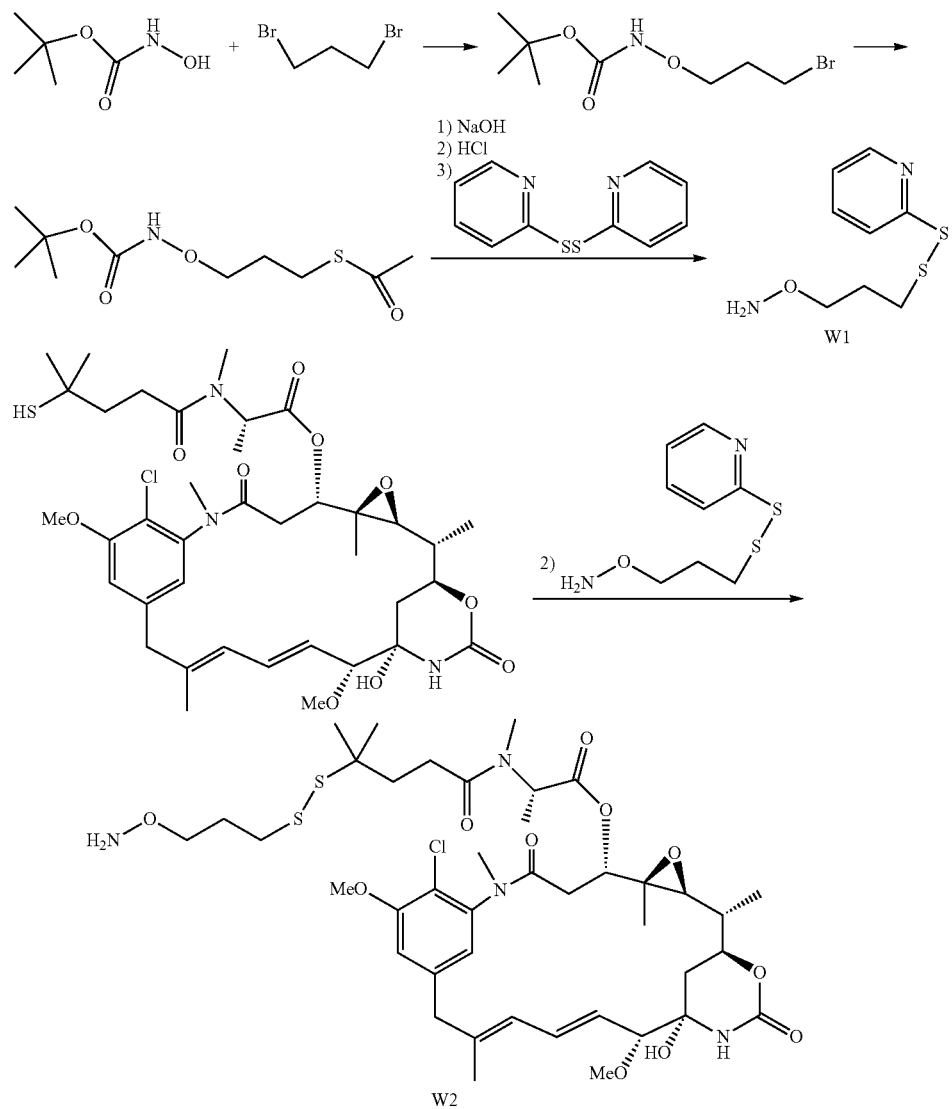

Boc-hydroxyl amine will be reacted with 1,3-dibromopropane then with thioacetic acid. The thiol and amine will be deprotected by treatment with NaOH followed by HCl then the thiol moeity will be reacted with 2,2'-dipyridyldisulfide to give W1. DM4 will be reacted with W1 to give W2. 1,3-dibromopropane can be replaced by other symetric dibromides to give spacers of other lengths between the DM and disulfide moities.

The linker W1 can also be used to derivatize a ketone or aldehyde-bearing cell binding agent to introduce a reactive disulfide. The oxime can also be optionally reduced. Either method will allow the addition of a thiol bearing maytansinoid such as DM1 or DM4 to complete the conjugation.

Example 8

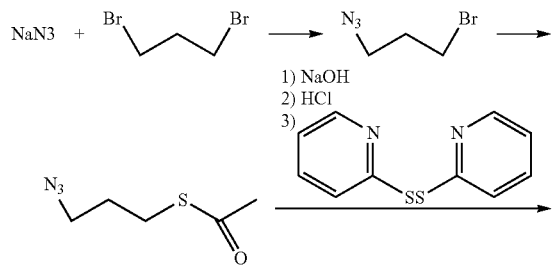

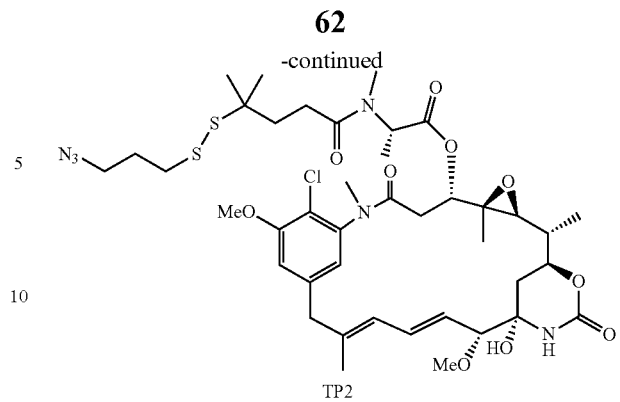

Sodium azide can be reacted with 1,3-dibromopropane then with thioacetic acid. The thiol can be deprotected by treatment with NaOH followed by HCl then the thiol moeity can be reacted with 2,2'-dipyridyldisulfide to give TP1. DM4 can be reacted with TP1 to give TP2. 1,3-dibromopropane can be replaced by other symetric dibromides to give spacers of other lengths between the DM and disulfide moities.

The linker TP1 can also be used to derivatize an alkyne-bearing cell binding agent to introduce a reactive disulfide. Addition of a thiol bearing maytansinoid such as DM1 or DM4 would then complete the conjugation.

Alternatively the reactive disulfide of the cell binding agent modified with linker TP1 can be reduced with reagents such as DTT or TCEP then the resulting thiol can be reacted with a maytansinoid bearing a reactive disulfide such as PyS-DM1 or PyS-DM4.

Example 9

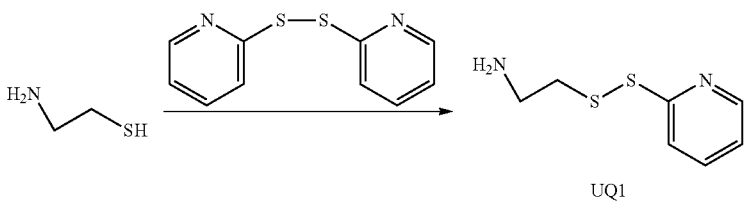

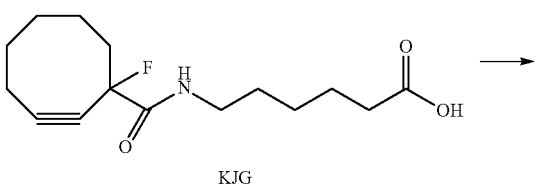

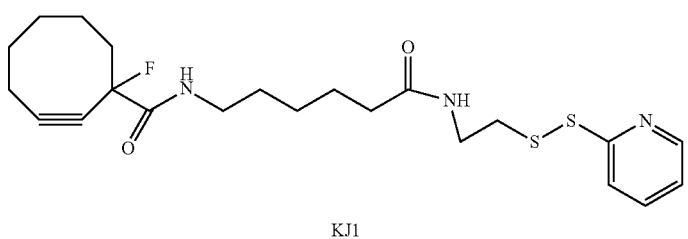

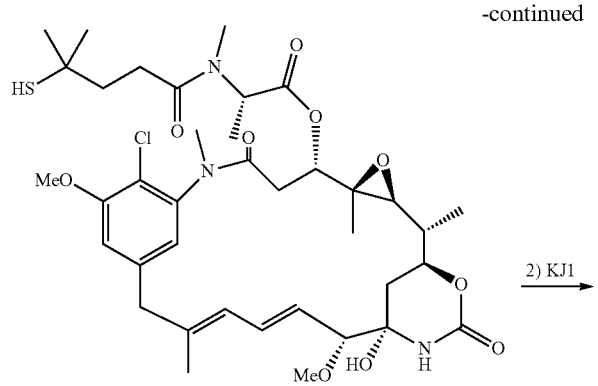

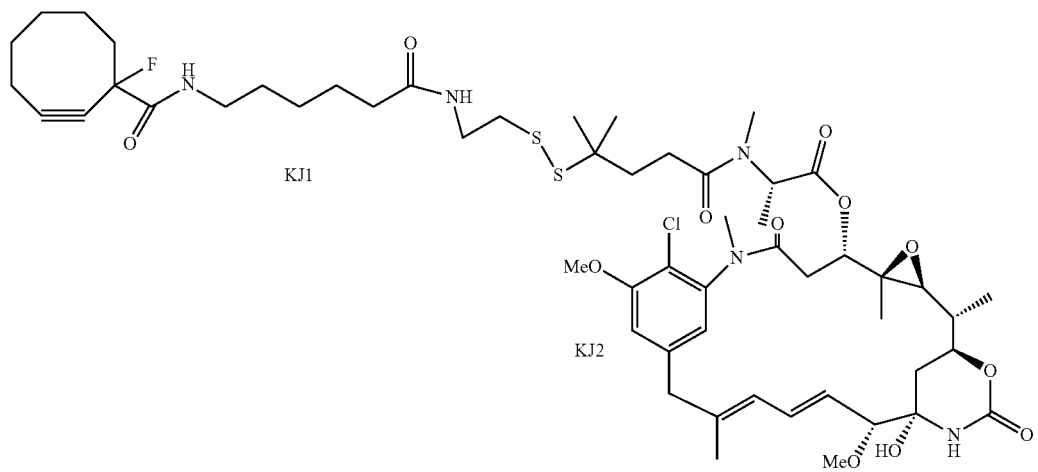

2-mercapto-1-ethylamine can be reacted with 2,2'-dithiopyridine then with a carboxylic acid bearing cyclooctyne such as KJG to give a linker KJ1. The linker can then be reacted with a thiol-bearing maytansinoid such as DM1 or DM4 to give a compound that can be conjugated to an azide-bearing cell binding agent.

The linker bearing a reactive disulfide and a cyclooctyne can alternatively be reacted with an azide-bearing cell binding agent then reacted with a thiol-bearing maytansinoid such as DM1 or DM4.

The linker KJ1 bearing a reactive disulfide and a cyclooctyne can alternatively be reacted with an azide-bearing cell binding agent then the reactive disulfide can be reduced with a reagent such as dithiothreitol or TCEP to give a cell binding agent bearing one or more newly formed thiol groups. The resulting molecule can then be reacted with a maytansinoid bearing a reactive disulfide such as PyS-DM1 or PyS-DM4

Example 10

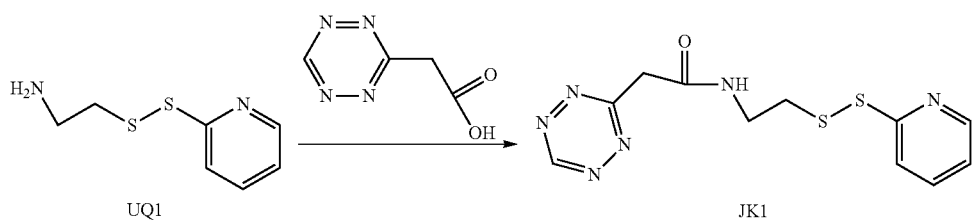

-continued

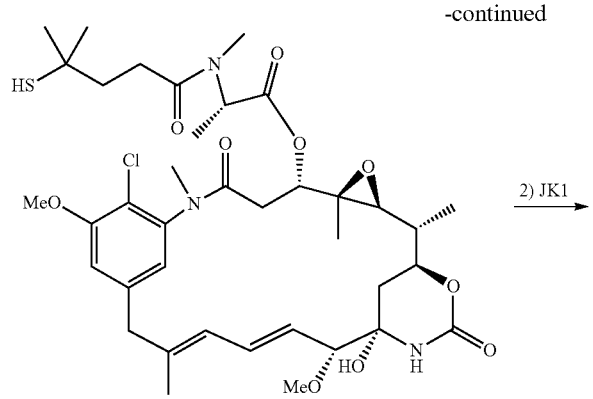

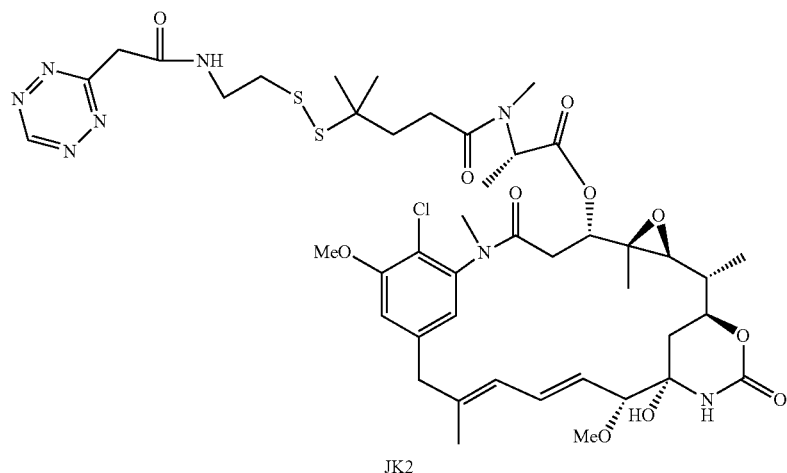

JK2

UQ1 can be reacted with a tetrazene bearing a carboxylic acid such as 1,2,4,5-Tetrazine-3-acetic acid to give a linker such as linker JK1. The linker can then be reacted with a thiol-bearing maytansinoid such as DM1 or DM4 to give a compound such as JK2 that can be conjugated to a cell binding agent that bears a strained alkene such as a norbornene or a trans-cyclooctene.

The linker JK1 bearing a reactive disulfide and a tetrazine can alternatively be reacted with a cell binding agent bearing a strained alkene such as a norbornene or a trans-cyclooctene then reacted with a thiol-bearing maytansinoid such as DM1 or DM4 to give a conjugate such as JK2.

The cell binding agent modified with a reactive disulfide can alternatively be reduced to cleave the reactive disulfide giving a thiol which can in turn be reacted with a thiol-bearing maytansinoid such as DM1 or DM4 to give a conjugate such as JK2.

Example 11

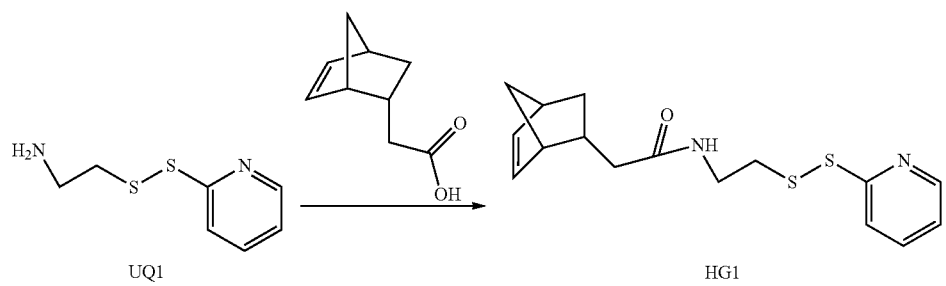

UQ1       HG1

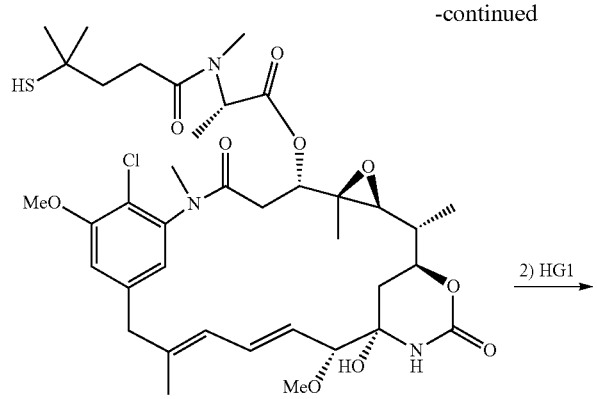

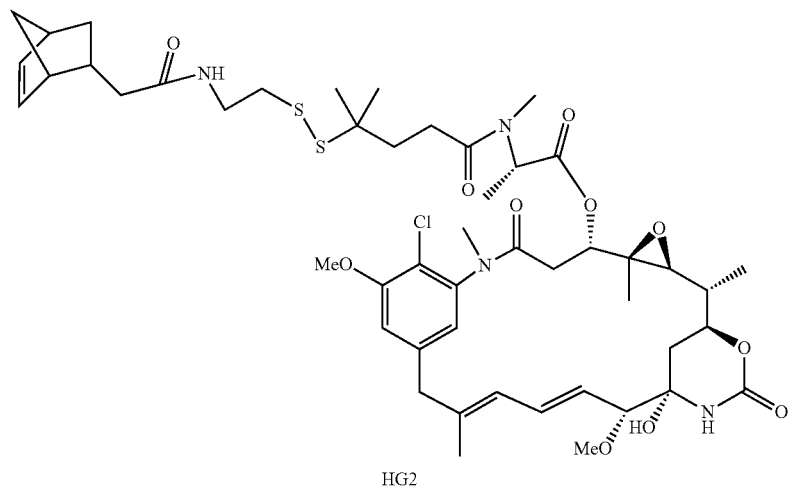

HG2

UQ1 can be reacted with a Norbornene or other strained alkene bearing a carboxylic acid such as (1S,2S,4S)-bicyclo[2.2.1]hept-5-en-2-ylacetic acid to give a linker such as linker HG1. The linker can then be reacted with a thiol-bearing maytansinoid such as DM1 or DM4 to give a compound such as HG2 that can be conjugated to a cell binding agent that bears a tetrazine.

The linker bearing a reactive disulfide and a strained alkene can alternatively be reacted with a cell binding agent bearing a tetrazine then reacted with a thiol-bearing maytansinoid such as DM1 or DM4 to give a conjugate such as HG2.

The cell binding agent modified with a reactive disulfide can alternatively be reduced to cleave the reactive disulfide giving a thiol which can in turn be reacted with a thiol-bearing maytansinoid such as DM1 or DM4 to give a conjugate such as HG2.

Example 12

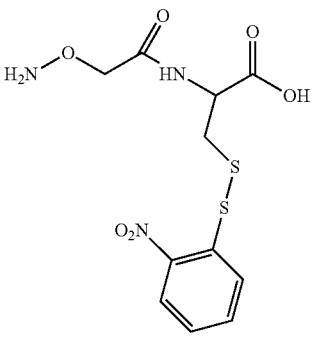

-continued

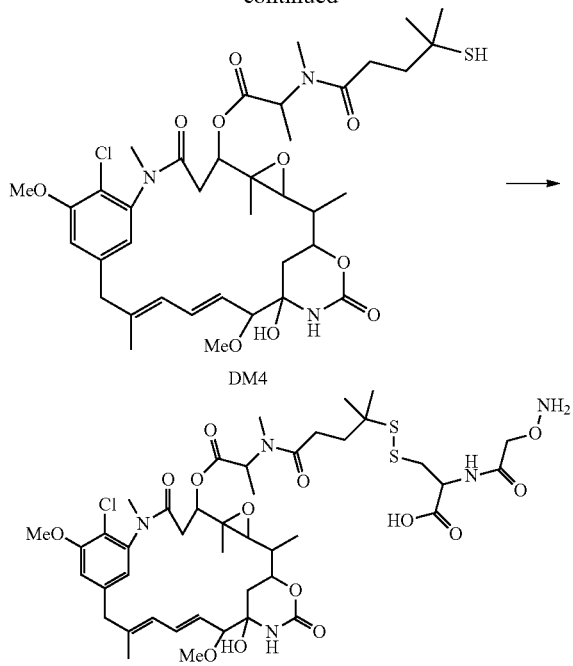

Alkoxaminoacetyl-Cys(S-2-NO2-Phenyl)—OH (1 mg, 2.88 µmol, prepared as previously described Org. Biomol. Biochem. 2006, 4, 1313-1419) and DM4 (6 mg, 7.7 µmol) were dissolved in DMF (250 µL) and deionized water (25 µL) and magnetically stirred for 1 h. The reaction mixture was HPLC purified using a 21×150 mm C18 column eluting at 20 mL/min with 95% deinized water containing 0.1% formic acid and an acetonitrile gradient of 5%-95% over 30 min. Desired product was collected, frozen and lyophilized to give approximately 0.25 mg (9% yield) of desired product as a white solid. MS (M+H)$^+$ found 972.5; calcd. 972.3; MS (M−1) found 970.4; calcd. 970.3. $^1$H NMR (400 MHz, DMSO-d6) δ 0.78 (s, 3H), 1.08 (s, 3H), 1.12 (s, 5H), 1.16 (d, J=6.7 Hz, 3H), 1.25 (d, J=14.6 Hz, 2H), 1.44 (d, J=12.4 Hz, 3H), 1.58 (s, 3H), 1.60-1.71 (m, 2H), 1.80 (d, J=2.4 Hz, 3H), 1.89 (d, J=2.0 Hz, 3H), 2.00-2.06 (m, 1H), 2.20 (d, J=11.9 Hz, 2H), 2.67 (dt, J=4.0, 1.9 Hz, 1H), 2.71 (s, 3H), 2.80 (d, J=9.6 Hz, 1H), 3.10 (s, 3H), 3.43-3.51 (m, 2H), 3.79 (s, 1H), 3.94 (s, 3H), 4.06 (t, J=11.2 Hz, 1H), 4.29 (d, J=3.2 Hz, 2H), 4.53 (dd, J=12.0, 2.9 Hz, 1H), 5.32 (q, J=6.9 Hz, 1H), 5.60 (dd, J=14.5, 9.2 Hz, 1H), 5.93 (s, 1H), 6.48-6.56 (m, 2H), 6.59 (t, J=10.6 Hz, 1H), 6.85 (s, 1H), 7.19 (d, J=1.8 Hz, 1H), 7.51 (d, J=5.8 Hz, 1H), 8.33 (s, 1H).

Example 13

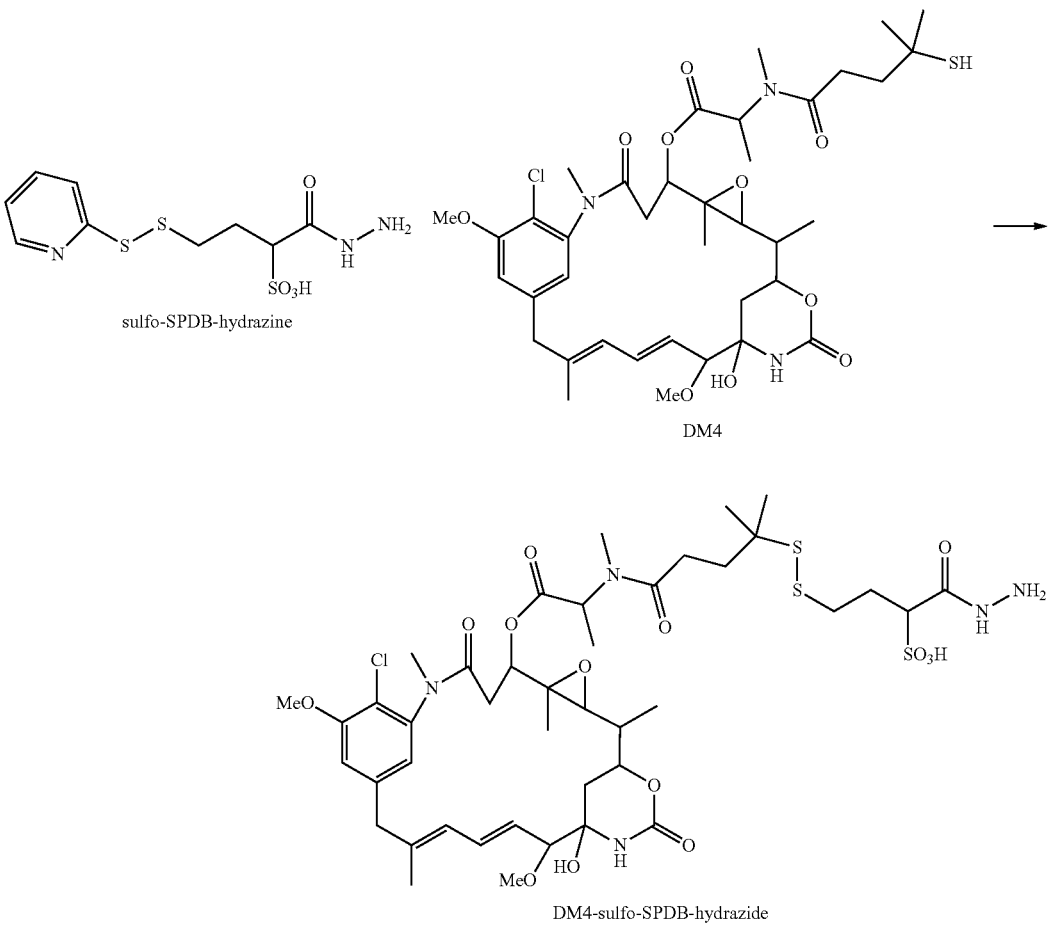

Sulfo-SPDB-hydrazine (1 mg, 3.1 μmol) and DM4 (4 mg, 5.1 μmol) were dissolved in DMF (300 μL) and ¼th saturated aqueous sodium bicarbonate (100 μL) and magnetically stirred for 1 hour. The reaction mixture was HPLC purified using a 21×150 mm C18 column eluting at 20 mL/min with 95% deinoized water containing 0.1% formic acid and an acetonitrile gradient of 5%-95% over 30 min. Desired product was collected, frozen and lyophilized to give approximately 1 mg (19% yield) of desired product as a white solid. MS (M+H)$^+$ found 992.6, calcd. 992.3; MS (M−1) found 990.5, calcd. 990.3.

I claim:

1. A linker compound represented by the following formula, or a salt thereof:

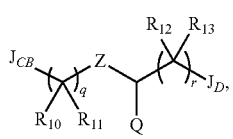
(V)

wherein:
- $J_{CB}$ is maleimide;
- Z is —C(=O)—NR$_9$— or —NR$_9$—C(=O)—;
- Q is H or SO$_3$H or a salt thereof, provided that when Z is —C(=O)—NR$_9$—, Q is —SO$_3$H;
- R$_9$, R$_{10}$, R$_{11}$, R$_{12}$, and R$_{13}$, for each occurrence, are independently H or an optionally substituted alkyl;
- q and r, for each occurrence, are independently an integer between 0 and 10; and
- $J_D$ is —SH, or —SSR$^d$, wherein R$^d$ is phenyl, nitrophenyl, dinitrophenyl, carboxynitrophenyl, pyridyl or nitropyridyl.

2. The linker compound of claim 1, wherein R$_9$ is H.

3. A linker compound represented by following formula, or a salt thereof:

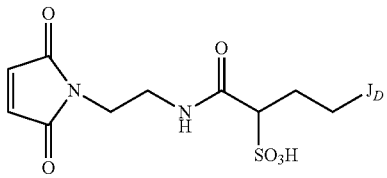

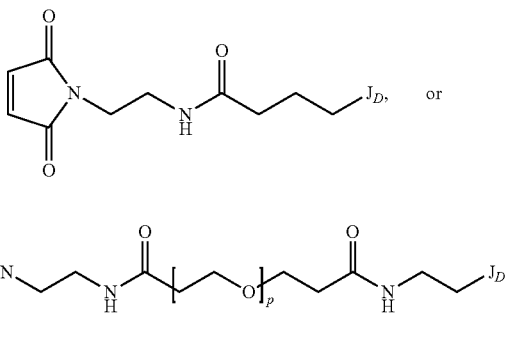

wherein $J_D$ is —SSR$^d$; R$^d$ is phenyl, nitrophenyl, dinitrophenyl, carboxynitrophenyl, pyridyl or nitropyridyl; and p is an integer from 2 to 8.

4. The linker compound of claim 3, represented by the following formula, or a salt thereof:

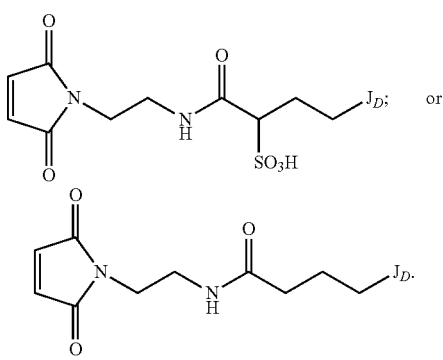

5. The linker compound of claim 1, wherein Z is —NR$_9$—C(=O)—; and Q is H or SO$_3$H.

* * * * *